(12) United States Patent
Oberli et al.

(10) Patent No.: US 11,179,180 B2
(45) Date of Patent: Nov. 23, 2021

(54) DEFORMABLE THREADED LOCKING STRUCTURES, AND RELATED SYSTEMS AND METHODS

(71) Applicant: DePuy Synthes Products, Inc., Raynham, MA (US)

(72) Inventors: Joel Oberli, Niederdorf (CH); This Aebi, Grenchen (CH); Mirko Rocci, Bettlach (CH); Johanna F. Menze, Zurich (CH); Said Ghammar, Zuchwil (CH)

(73) Assignee: DePuy Synthes Products, Inc., Raynham, MA (US)

( * ) Notice: Subject to any disclaimer, the term of this patent is extended or adjusted under 35 U.S.C. 154(b) by 362 days.

(21) Appl. No.: 16/437,105

(22) Filed: Jun. 11, 2019

(65) Prior Publication Data
US 2020/0390483 A1 Dec. 17, 2020

(51) Int. Cl.
*A61B 17/80* (2006.01)
*A61L 31/02* (2006.01)
(Continued)

(52) U.S. Cl.
CPC ...... *A61B 17/8057* (2013.01); *A61B 17/8052* (2013.01); *A61L 31/022* (2013.01); *A61L 31/14* (2013.01); *A61B 2017/00946* (2013.01)

(58) Field of Classification Search
CPC .............. A61B 17/8057; A61B 17/8052
See application file for complete search history.

(56) References Cited

U.S. PATENT DOCUMENTS 6,669,701 B2   12/2003   Steiner et al.
6,719,759 B2    4/2004   Wagner et al.
(Continued)

FOREIGN PATENT DOCUMENTS

EP        2919688 A1    9/2015
WO     2006/014436 A1   2/2006
(Continued)

OTHER PUBLICATIONS

U.S. Appl. No. 63/107,699, filed Oct. 30, 2020 entitled Bone Plates Having Multi-Use Screw Holes for Locking and Compression Screws, and Related Systems and Methods.
(Continued)

*Primary Examiner* — Andrew Yang
(74) *Attorney, Agent, or Firm* — BakerHostetler

(57) ABSTRACT

A bone fixation system includes a plate body that defines an interior surface that defines at least one hole defining a central axis. The internal surface defines plate threads within the hole. The system includes a bone screw having a shaft extending from head along a central axis, wherein the head has an exterior surface that defines threads that are configured to threadedly engage the plate threads. The plate threads and head threads each have a cross-sectional profile in a respective reference plane extending along the respective central axis. The cross-sectional profiles each comprise roots, crests, and flanks extending therebetween. The roots, crests, and flanks collectively deviate from a reference cross-sectional profile that is V-shaped in the respective reference plane and defines crest reference points at apices at a first side thereof and root reference points at apices at a second side thereof opposite the first side. Such deviation causes a thread height measured from the crests to the roots to be less than a reference height measured from the crest reference points to the root reference points, such that a ratio
(Continued)

of the thread height of the head threads to the reference height of the head threads is from 0.50:1 to 0.80:1, and a ratio of the thread height of the plate threads to the reference height of the plate threads is from 0.50:1 to 1.00:1.

23 Claims, 28 Drawing Sheets

(51) Int. Cl.
*A61L 31/14* (2006.01)
*A61B 17/00* (2006.01)

(56) References Cited

U.S. PATENT DOCUMENTS

| | | | |
|---|---|---|---|
| 7,354,441 | B2 | 4/2008 | Frigg |
| 7,695,502 | B2 | 4/2010 | Orbay et al. |
| 7,776,076 | B2 | 8/2010 | Grady et al. |
| 7,951,176 | B2 | 5/2011 | Grady et al. |
| 7,976,570 | B2 | 7/2011 | Wagner et al. |
| 8,343,196 | B2 | 1/2013 | Schneider |
| 8,758,346 | B2 | 6/2014 | Koay et al. |
| 8,845,698 | B2 | 9/2014 | Schneider |
| 8,852,245 | B2 | 10/2014 | Schneider |
| 8,876,873 | B2 | 11/2014 | Schneider |
| 8,940,029 | B2 | 1/2015 | Leung et al. |
| 9,107,711 | B2 | 8/2015 | Hainard |
| 9,161,791 | B2 | 10/2015 | Frigg |
| 9,295,505 | B2 | 3/2016 | Schneider |
| 9,308,034 | B2 | 4/2016 | Grady et al. |
| 9,314,284 | B2 | 4/2016 | Chan et al. |
| 9,931,148 | B2 | 4/2018 | Grady et al. |
| 10,231,768 | B2 | 3/2019 | Grady et al. |
| 10,342,586 | B2 | 7/2019 | Schneider |
| 10,653,466 | B2 | 5/2020 | Grady et al. |
| 10,772,665 | B2 | 9/2020 | Bosshard et al. |
| 2016/0367299 | A1 | 12/2016 | Paolino et al. |
| 2019/0269444 | A1 | 9/2019 | Schneider |
| 2019/0328430 | A1 | 10/2019 | Bosshard et al. |
| 2020/0237420 | A1 | 7/2020 | Grady et al. |
| 2020/0390483 | A1 | 12/2020 | Oberli et al. |
| 2021/0015526 | A1 | 1/2021 | Oberli et al. |

FOREIGN PATENT DOCUMENTS

| | | |
|---|---|---|
| WO | 2013/036362 A1 | 3/2013 |
| WO | 2014/078289 A1 | 5/2014 |

OTHER PUBLICATIONS

Entitled Threaded Locking Structures for Affixing Bone Anchors to a Bone Plate, and Related Systems and Methods, filed Apr. 30, 2018, U.S. Appl. No. 15/966,047.

Entitled, Locking Structures for Affixing Bone Anchors to a Bone Plate, and Related Systems and Methods, filed Mar. 29, 2018, U.S. Appl. No. 15/940,761.

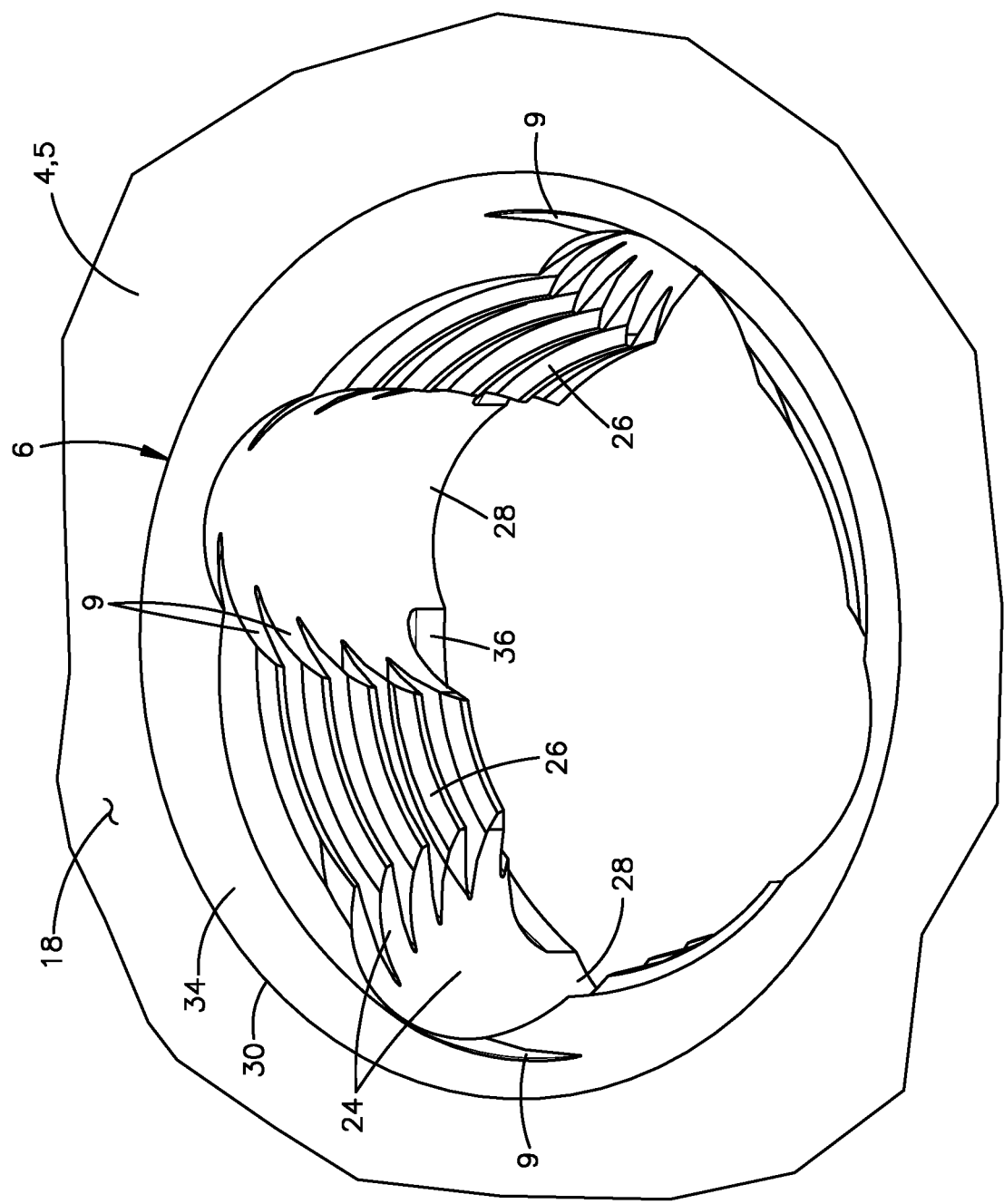

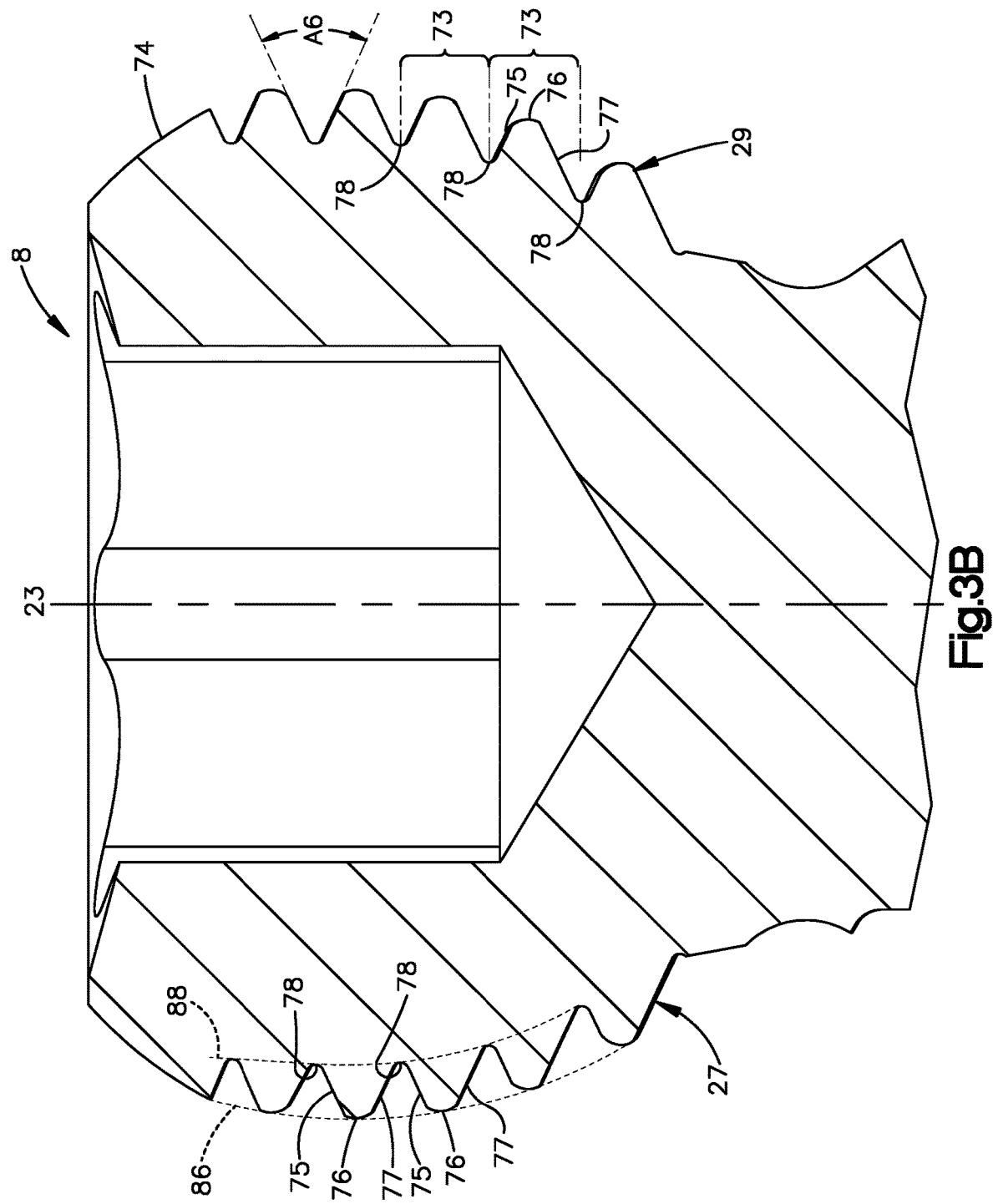

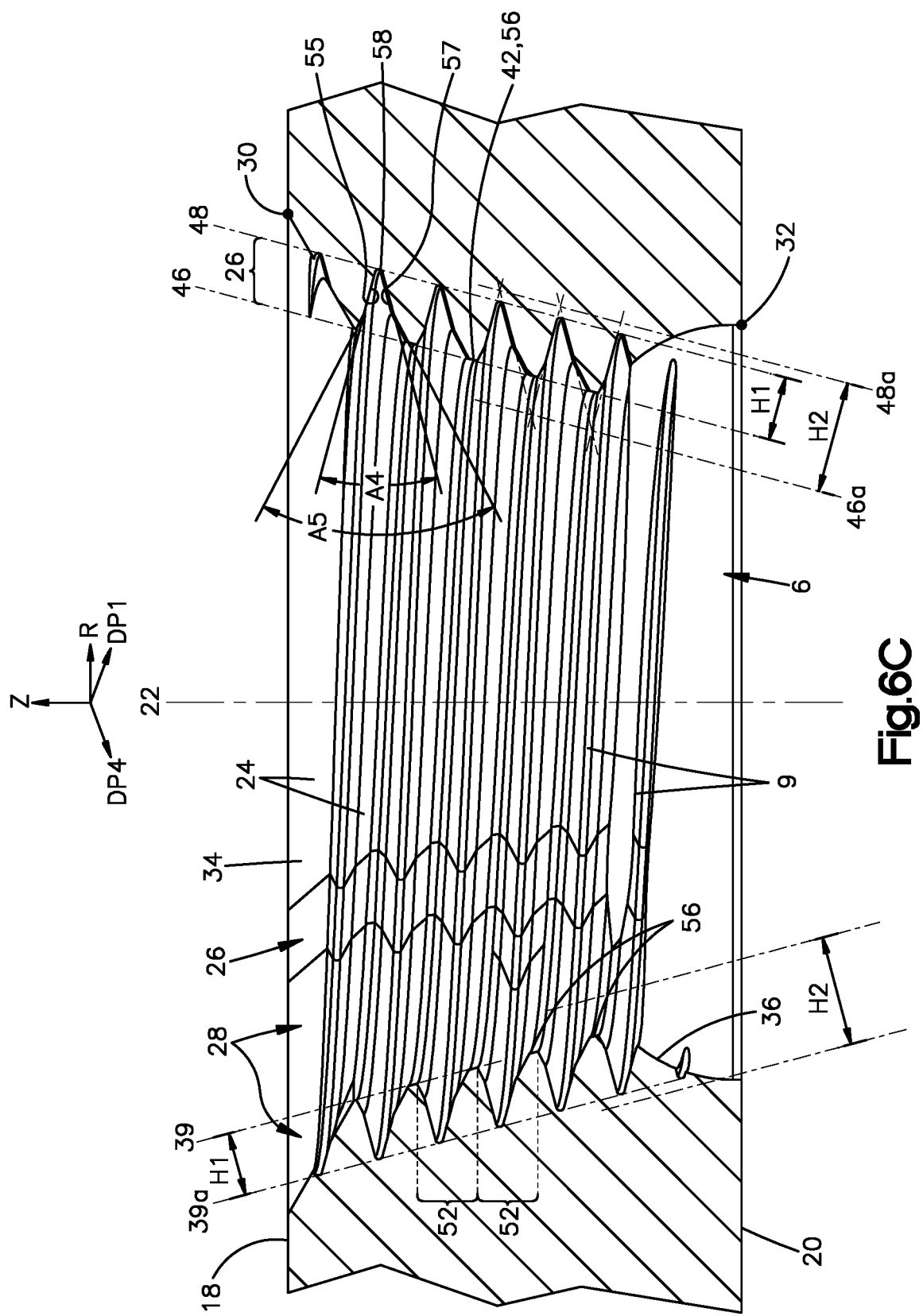

US 11,179,180 B2

DEFORMABLE THREADED LOCKING STRUCTURES, AND RELATED SYSTEMS AND METHODS

TECHNICAL FIELD

The present invention relates to bone plates and bone anchors for coupling to the bone plates, and particularly relates to threaded locking structures defined within a fixation hole of a bone plate and complimentary threaded locking structures defined on a head of a bone anchor.

BACKGROUND

Bone plate systems for the internal fixation of bone fractures are well known. Conventional bone plate systems are particularly well-suited to promote the healing of a fracture. A bone anchor, such as a bone screw, is inserted through a fixation aperture or hole in a bone plate and is threaded into bone to compress, neutralize, buttress, tension, band, and/or bridge the fracture ends together. Bone screws that are capable of locking with the bone plate can be employed to transfer loads from one fractured bone part, over a plate, and onto another fractured bone part without drawing the bone against the plate, and to avoid loosening or backing out the bone screws with respect to the plate (which can lead to poor alignment and poor clinical results). One known embodiment of such a screw employs a screw head with external threads for engaging with a corresponding thread on the inner surface of a fixation hole to lock the screw to the plate. These screws, which are hereinafter referred to as "locking screws" or "compression screws", and which can include standard-type locking screws that are configured to lock within fixation hole substantially only at a "nominal" orientation whereby the central screw axis is substantially aligned with the central hole axis, as well as "variable-angle" (VA) locking screws that are configured to lock within a fixation hole at either a nominal orientation or an "angulated" orientation whereby the central screw axis is oriented at an acute angle with respect to the respective central hole axis.

SUMMARY

According to an embodiment of the present disclosure, a bone fixation system includes a plate body that defines an interior surface that defines at least one hole defining a central axis. The internal surface defines plate threads within the hole. The system includes a bone screw having a shaft extending from head along a central axis, wherein the head has an exterior surface that defines threads that are configured to threadedly engage the plate threads. The plate threads and head threads each have a cross-sectional profile in a respective reference plane extending along the respective central axis. The cross-sectional profiles each comprise roots, crests, and flanks extending therebetween. The roots, crests, and flanks collectively deviate from a reference cross-sectional profile that is V-shaped in the respective reference plane and defines crest reference points at apices at a first side thereof and root reference points at apices at a second side thereof opposite the first side. Such deviation causes a thread height measured from the crests to the roots to be less than a reference height measured from the crest reference points to the root reference points, such that a ratio of the thread height of the head threads to the reference height of the head threads is from 0.50:1 to 0.80:1, and a ratio of the thread height of the plate threads to the reference height of the plate threads is from 0.50:1 to 1.00:1.

BRIEF DESCRIPTION OF THE DRAWINGS

The foregoing summary, as well as the following detailed description of illustrative embodiments of the present application, will be better understood when read in conjunction with the appended drawings. For the purposes of illustrating the locking structures of the present application, there is shown in the drawings illustrative embodiments. It should be understood, however, that the application is not limited to the precise arrangements and instrumentalities shown. In the drawings:

FIG. 2A is a perspective view of a locking hole of the bone plate illustrated in FIGS. 1A and 1B;

FIG. 3B is a sectional side view of the VA locking screw illustrated in FIG. 3A, taken along the central axis of the screw;

FIG. 6C is a sectional side view of the locking hole taken along section line 6C-6C shown in FIG. 6B, illustrating the threaded locking structure of the hole;

DETAILED DESCRIPTION OF ILLUSTRATIVE EMBODIMENTS

Figure 1A:
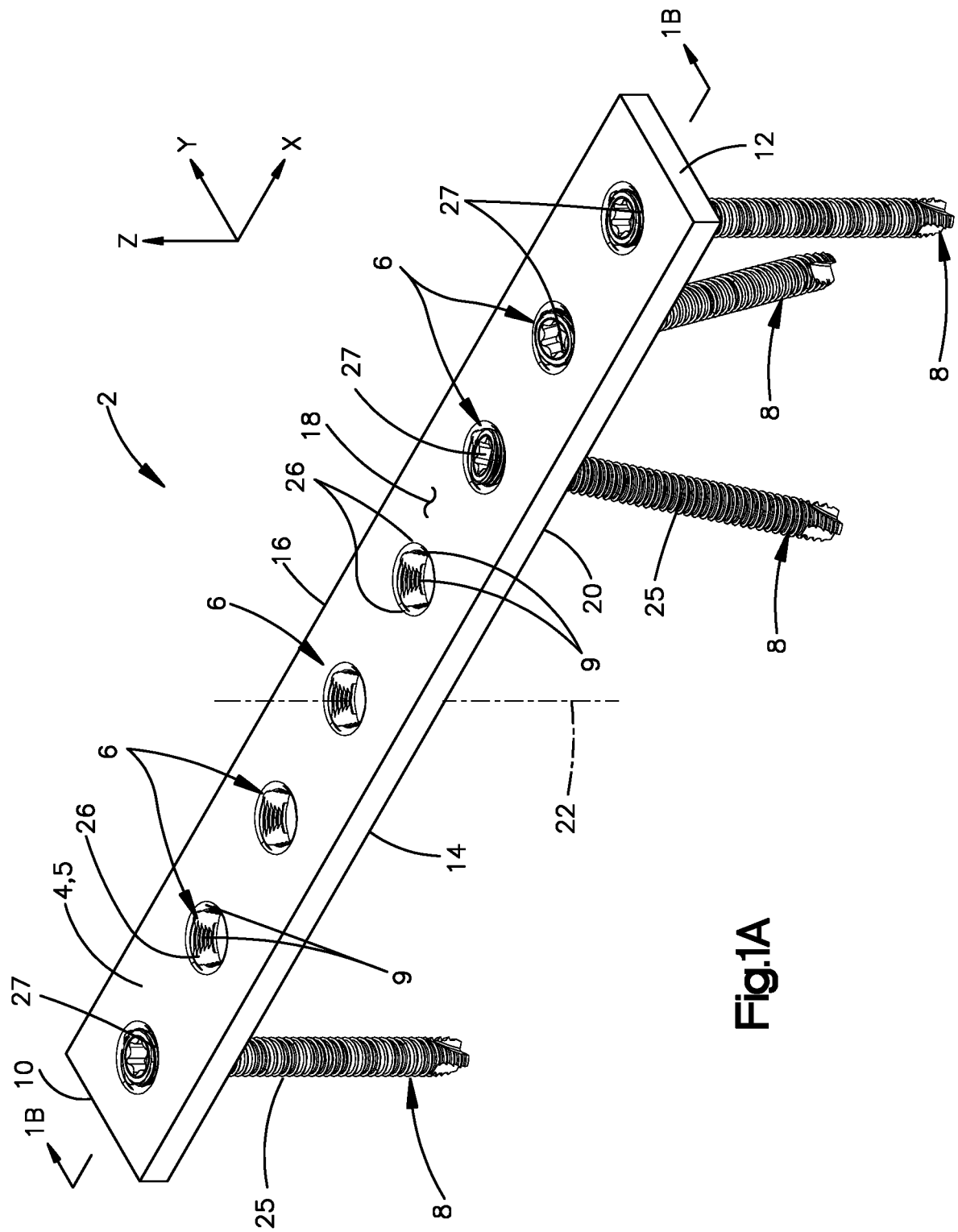
FIG. 1A is a perspective view of a bone fixation system that includes a bone plate and a plurality of locking screws disposed within locking holes of the bone plate, according to an embodiment of the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately" and "substantially", as used herein with respect to dimensions, angles, and other geometries, takes into account manufacturing tolerances. Further, the terms "approximately" and "substantially" can include 10% greater than or less than the stated dimension or angle. Further, the terms "approximately" and "substantially" can equally apply to the specific value stated.

Variable angle (VA) locking screws have a tendency to cause, as well as exhibit, cross-threading within a locking hole in which they are inserted, particularly when the VA locking screw is inserted in the locking hole at an angulated trajectory. Cross-threading of the plate threads can be caused by the external threads on the screw head not fitting within (i.e., interfering with) and thus cross-threading the internal threads of the locking hole. Such thread interference can also cause cross-threading of the external threads of the screw head. Regions of contact between the crests of the screw head threads and portions of the internal threads, particularly at or near the crests of the internal threads at angulation, can be particularly susceptible to cross-threading. Cross-threading is problematic because it reduces the intended interference fit (also referred to as the "form-fit") between the screw head threads and the internal threads of the locking hole, which can reduce stability and mechanical strength at the locked interface between the screw head and the locking hole.

The embodiments disclosed herein pertain to locking structures employed within a locking hole and complimentary locking structures on the head of a locking screw. These complimentary locking structures define mating threads having complimentary geometries that provide enhanced control over the deformation of the mating threads, particularly over the deformation of the internal threads of the locking hole, which will effectively become re-aligned to the screw axis at angulated insertions. Such favorable geometries include the respective cross-sectional profiles (referred to in the art as "thread-forms") of the screw head threads and the plate hole threads. These complimentary geometries and profiles can be collectively characterized as "thread proportions" of the plate and screw threads. One way in which the thread profiles disclosed herein control the thread deformation is by providing the screw head threads with a stronger (e.g., larger) profile and interfacing it against an intentionally more malleable (e.g., thinner) profile of the plate hole threads. Another way in which thread deformation is controlled is by adjusting the edge geometry of the thread profiles, such as at the thread crests, to reduce undesirable mechanical interference at the thread interface at angulated screw orientations. The thread proportions disclosed herein have been shown to avoid or reduce cross-threading at angulated screw insertions, and also when the screw insertion involves "timing error", which is an axial mis-alignment of the screw head threads relative to the plate hole threads. Thus, the threaded locking structures described herein can lock with the heads of VA locking screws at angulation, as well as both VA and standard-type locking screws at nominal orientations, in a manner that inhibits (or at least reduces) cross-threading, or at least substantially causes any cross-threading to occur substantially entirely within the plate threads as an act of plastic and elastic thread deformation. The threaded locking structures described herein have also been demonstrated to increase the overall cantilever strength at the locking thread interface.

Referring to FIG. 1A, a bone fixation system 2 includes a bone plate 4 having a plate body 5 that defines therein one or more fixation holes, such as variable-angle (VA) locking holes 6. The VA locking holes 6 are configured to receive anchor members, such as locking screws 8, for example, that are configured to affix the bone plate 4 to one or more portions of bone. The plate body 5 defines internal threads 9 within the VA locking holes 6. Accordingly, the internal threads 9 can also be referred to as "plate hole threads" or simply "plate threads" or "hole threads." The plate threads 9 traverse locking structures, such as columns 26, defined within the VA locking holes 6. Thus the columns 26 can be referred to as "threaded columns". The threaded columns 26 are configured such that, during insertion of a locking screw 8 within the VA locking hole 6, a screw shaft 25 of the locking screw 8 bypasses the columns 26, which in turn engage external threads 29 on the screw head 27 of the locking screw 8 in a manner providing enhanced locking engagement between the locking screw 8 and the bone plate 4, as set forth in more detail below.

The bone plate 4 can be a bridge plate, as shown, although other bone plate types and configurations are within the scope of the present disclosure. The plate body 5 can define a first end 10 and a second end 12 spaced from each other along a longitudinal direction X and a first lateral side 14 and a second lateral side 16 spaced from each other along a lateral direction Y that is substantially perpendicular to the longitudinal direction X. The bone plate 4 can also define an upper plate surface 18 configured to face away from the bone and an opposed lower plate surface 20 configured to face the bone. The upper and lower plate surfaces 18, 20 are spaced from each other along a vertical direction Z substantially perpendicular to each of the longitudinal direction X and the lateral direction Y. It is to be appreciated that, as used herein, the terms "longitudinal", "longitudinally", and derivatives thereof refer to the longitudinal direction X; the terms "lateral", "laterally", and derivatives thereof refer to the lateral direction Y; and the terms "vertical", "vertically", and derivatives thereof refer to the vertical direction Z.

The VA locking holes 6 extend from the upper plate surface 18 to the lower plate surface 20 along a central hole axis 22. The central hole axis 22 is oriented along an axial hole direction. As used herein, the term "axial direction" (e.g., "axial hole direction" and "axial screw direction") is defined as the direction along which the respective axis extends. Furthermore, the directional terms "axial", "axially", and derivatives thereof refer to the respective axial direction. Thus, as used herein, the directional term "axially upward" and derivatives thereof refers to the axial hole direction from the lower plate surface 20 toward the upper plate surface 18. Conversely, the term "axially downward" and derivatives thereof refers to the axial hole direction from the upper plate surface 18 toward the lower plate surface 20. Thus, "axially upward" and "axially downward" are each mono-directional components of the "axial direction", which is bi-directional. In the embodiments depicted in the Figures, the axial hole direction (and thus also the central hole axis 22) is oriented along the vertical direction Z. Accordingly, the axial hole direction is also denoted by "Z" throughout this disclosure. It should be appreciated, however, that the scope of the present disclosure covers embodiments in which the axial hole direction (and thus also the central hole axis 22) of the is offset from the vertical direction Z at an oblique angle. It should also be appreciated that when the terms "axially upper", "axially lower," and the like are used with reference to the VA locking screw 8, such terms refer to a central axis 23 of the screw 8, particularly as it would be oriented within the VA locking hole 6.

The plate body 5 and the locking screws 8 can each comprise one or more biocompatible materials. By way of non-limiting examples, the plate body 5 can be formed of a material selected from a group comprising titanium, titanium alloys (e.g., titanium-aluminum-niobium (TAN) alloys, such as Ti-6Al-7Nb, and titanium-aluminum-vanadium (TAV) alloys), stainless steel, cobalt base alloys (e.g., cobalt-chrome alloys), composite materials, and polymeric materials and/or ceramic materials. Also by way of non-limiting examples, the locking screws 8 can be formed of a material selected from a group comprising titanium, titanium alloys (e.g., TAN alloys, TAV alloys, and nickel-titanium alloys, such as nitinol), stainless steel, cobalt base alloys (e.g., cobalt-chrome alloys), composite materials, and polymeric materials and/or ceramic materials. Preferably, the material of the locking screw 8 has a hardness that is greater than that of the material of the plate body 5. This parameter contributes to the locking characteristics described throughout the present disclosure. Preferably, the plate body 5 primarily or entirely comprises titanium and the locking screws 8 primarily or entirely comprise TAN. It should be appreciated, however, that other material compositions of the bone plates 4 and/or the locking screws 8 are within the scope of the present disclosure.

Furthermore, the dimensions set forth throughout this disclosure are made in reference to bone fixation systems 2 that includes at least one VA locking hole 6 and at least one VA locking screw 8 configured for nominal or angulated insertion within the at least one VA locking hole 6, in which the screw shaft 25 of the VA locking screw 8 defines a major diameter in a range of about 1.0 mm to about 5.0 mm, and more particularly a major diameter of about 3.5 mm, which can correspond to the threaded head 27 defining a major diameter of about 5.0 mm. It is to be appreciated, however, that any of the embodiments described below can be scaled upward or downward in size as needed for employment within larger or smaller bone fixation systems.

Figure 1B:
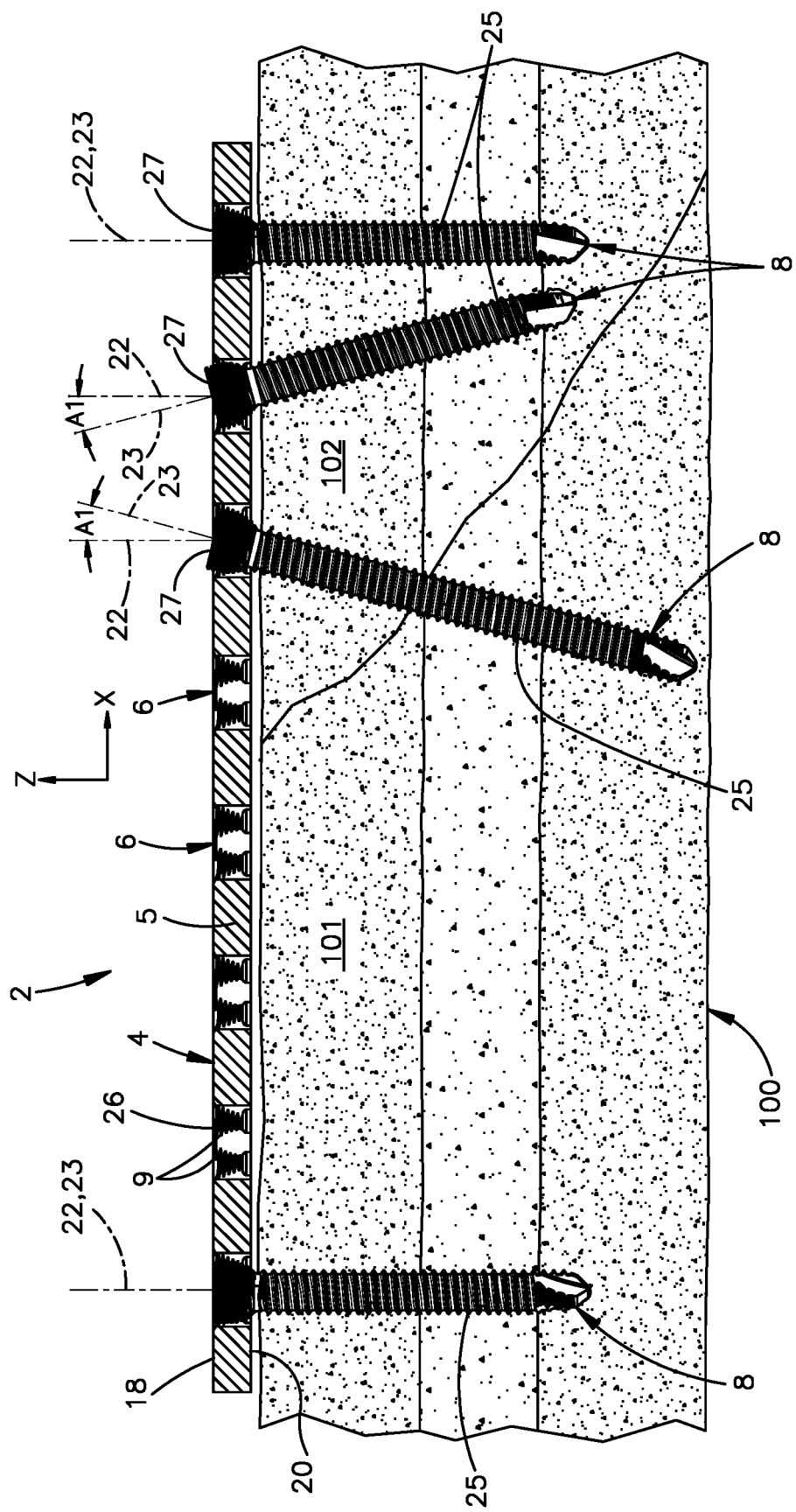
FIG. 1B is a sectional side view of the bone fixation system taken along section line 1B-1B in FIG. 1A affixed to a plurality of bone segments.

Referring now to FIG. 1B, the VA locking holes 6 can be configured to provide enhanced affixation with multiple types of locking screws 8, including VA locking screws 8 as well as standard-type locking screws, including such screws having various lengths, so as to allow a physician to implant the bone plate 4 to one or more bones or bone segments as desired. By way of non-limiting example, as shown, the bone plate 4 can be coupled to a long-bone 100 via locking screws 8 in a manner affixing fractured segments 101, 102 of the bone together. The VA locking holes 6 described herein can lock with VA locking screws 8 or standard-type locking screws at a nominal orientation whereby a central screw axis 23 thereof is substantially aligned with the central hole axis 22. The VA locking holes 6 can also lock with VA locking screws 8 at an angulated orientation whereby the central screw axis 23 is oriented at an acute angle A1 with respect to the respective central hole axis 22. Acute angle A1 can also be referred to as the "angle of angulation" or simply the "angulation." VA locking screws 8 and standard-type locking screws and their locking functionalities are described more fully in U.S. Pat. No. 9,314,284, issued Apr. 19, 2016, in the name of Chan et al. ("the '284 Reference"), and U.S. patent application Ser. No. 15/940,761, filed Mar. 29, 2018, in the name of Bosshard, et al. ("the '761 Reference"), and Ser. No. 15/966,047, filed Apr. 30, 2019, in the name of Bosshard, et al. ("the '047 Reference") the disclosures of each of which are hereby incorporated by reference as if set forth in their entireties herein.

During a bone plating operation, the screw shaft 25 of a locking screw 8 can be inserted through one of the VA locking holes 6 and driven into the underlying bone 100. In particular, rotation of the locking screw 8 causes its threaded screw head 27 to threadedly mate with the VA locking hole 6. As a result, the screw head 27 fastens the bone plate 4 to the underlying bone 100 substantially without applying a compressive force onto the bone plate 4 against the underlying bone 100. The bone plate 4 can be spaced from the underlying bone 100 when locked to the threaded screw head 27. Alternatively, the bone plate 4 can abut the underlying bone 100 when locked to the threaded screw head 27.

It is to be appreciated that, during a plating operation, the first locking screw 8 inserted through one of the VA locking holes 6 and into underlying bone 100 has the benefit of being able to generally mate with the plate threads 9 so that crests of the screw head thread 29 advance helically substantially along the roots of the plate threads 9. However, once the first locking screw 8 is locked to the bone plate 4 thereby fastening the plate 4 to the underlying bone 100, the subsequent locking screws 8 often lack the ability to have their external thread crests advance helically along the plate thread 9 roots. This results because, once the screw shafts 25 of these subsequent locking screws 8 advance through the VA locking holes 6 and threadedly purchase into the underlying bone 100, the relative axial positions of the screw head threads 29 and the plate threads 9 are substantially a function of the screw's threaded purchase with the underlying bone 100. This axial misalignment of the screw head threads 29 relative to the plate threads 9 is referred to herein as "timing error."

Figure 2B:
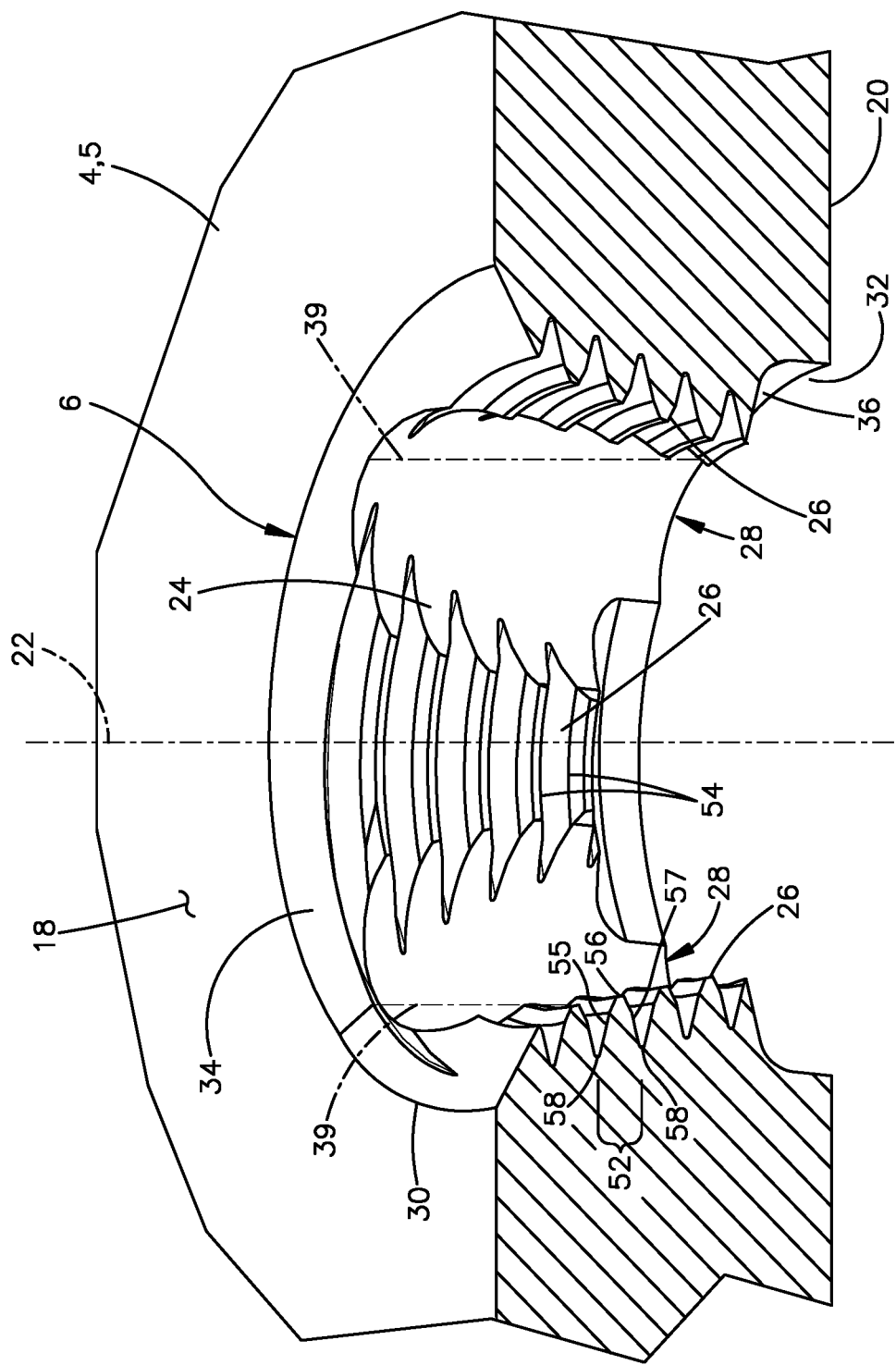
FIG. 2B is a sectional perspective view of the locking hole illustrated in FIG. 2A.
Figure 2C:
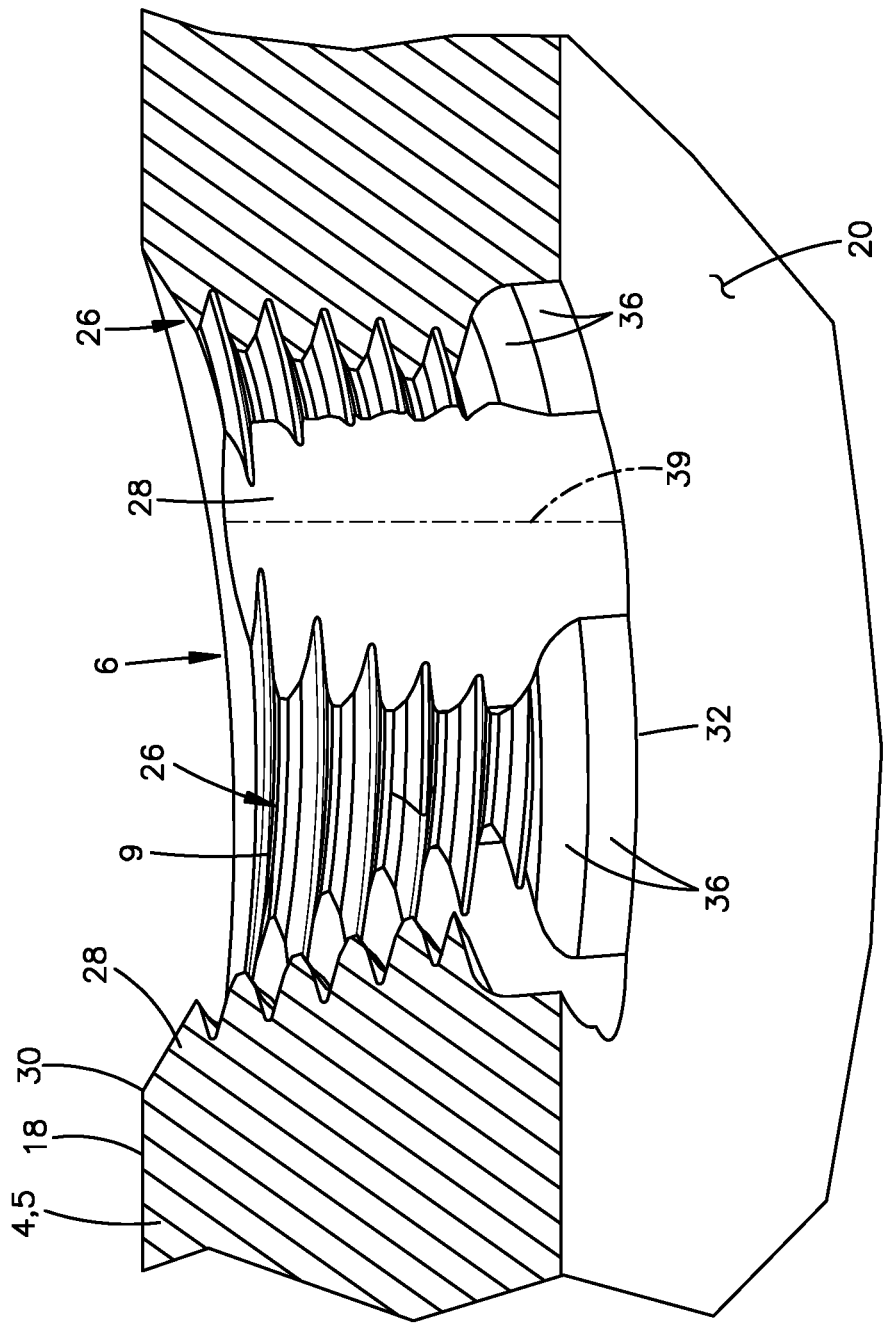
FIG. 2C is another sectional perspective view of the locking hole illustrated in FIG. 2A.

Referring now to FIGS. 2A through 2C, each of the VA locking holes 6 can be defined by an interior surface 24 of the plate body 5. Alternatively, the interior surface 24 can be defined by an insert plate body 5a fitted within an axial aperture or receptacle 95 of the plate body 5, as indicated in dashed lines in FIG. 2E. Typically, at least a portion of the interior surface 24 is tapered as it extends axially downward. Thus, the interior surface 24 is configured to prevent the screw head 27 from passing completely through the VA locking hole 6.

The interior surface 24 can define the threaded columns 26. The columns 26 extend axially between the upper and lower plate surfaces 18, 20. Within each (or at least some of) the VA locking holes 6, the columns 26 are sequentially located about a circumference of the interior surface 24. The interior surface 24 also defines a plurality of recesses 28 sequentially located circumferentially between the columns 26. The recesses 28 extend axially between the upper and lower plate surfaces 18, 20. The columns 26 and recesses 28 can be evenly spaced about the circumference of the interior surface 24 within the VA locking hole 6. However, in other embodiments, the columns 26 and/or recesses 28 can be un-evenly spaced about the circumference of the VA locking hole 6.

The plate threads 9 extend through the columns 26 and at least portions of the recesses 28 along one or more thread paths between the upper and lower plate surfaces 18, 20. As shown, the one or more thread paths can include a pair of non-intersecting thread paths (i.e., double-lead); however in other embodiments the one or more thread paths can include a single thread path (i.e., single-lead), or three or more thread paths (e.g., triple-lead, etc.). The thread paths are preferably helical, although other thread path types are within the scope of the present disclosure. As shown, portions of the recesses 28 can circumferentially interrupt the plate threads 9. Stated differently, the plate threads 9 can "bottom-out" along one or more and up all of the recesses 28. In other embodiments, however, the plate threads 9 can circumferentially traverse one or more and up to each of the recesses 28 in an uninterrupted fashion (i.e., the plate threads 9 need not bottom-out in the recesses 28).

The plate threads 9 have a cross-sectional profile in a reference plane that extends along the central hole axis 22. Such as cross-sectional profile is also referred to as a "thread-form," and includes crests 56, roots 58, and upper and lower flanks 55, 57 that extend between the crests 56 and roots 58, as shown in FIG. 2B. As used herein with reference to the plate threads 9, the term "crest" refers to the apex of a fully-developed thread-form. Each threaded column 26 defines one or more thread segments 52 extending along the thread path(s). As used herein, the term "thread segment" refers to any portion of a thread, such as the plate threads 9 and the screw head threads 29, that has a thread-form and a length along its thread path. The thread segments 52 of the plate threads 9 can also be referred to herein as "plate thread segments" 52. Plate thread segments 52 that traverse a column 26 can be referred to herein as "column threads" 54.

The interior surface 24 can define an upper perimeter 30 of the VA locking hole 6 at an interface with the upper plate surface 18 and a lower perimeter 32 of the VA locking hole 6 at an interface with the lower plate surface 20. The upper and lower perimeters 30, 32 can each be circular in shape, although other shapes are within the scope of the present disclosure, as discussed in more detail below. The interior surface 24 can also define one or more lead-in surfaces 34 that taper axially downward from the upper perimeter 30 to one or more of the columns 26. As shown, the one or more lead in surfaces 34 can include a single lead-in surface 34 can be circumferentially interrupted by one or more of the recesses 28. Alternatively, the lead-in surface 34 can extend circumferentially continuously and uninterrupted along a full revolution about the central hole axis 22. The interior surface 24 can also define an undercut surface 36 that tapers axially upward from the lower perimeter 32. The undercut surface 36 can extend circumferentially continuously and uninterrupted along a full revolution about the central hole axis 22. Alternatively, the undercut surface 36 can be circumferentially interrupted by one or more of the recesses 28.

Figure 2D:
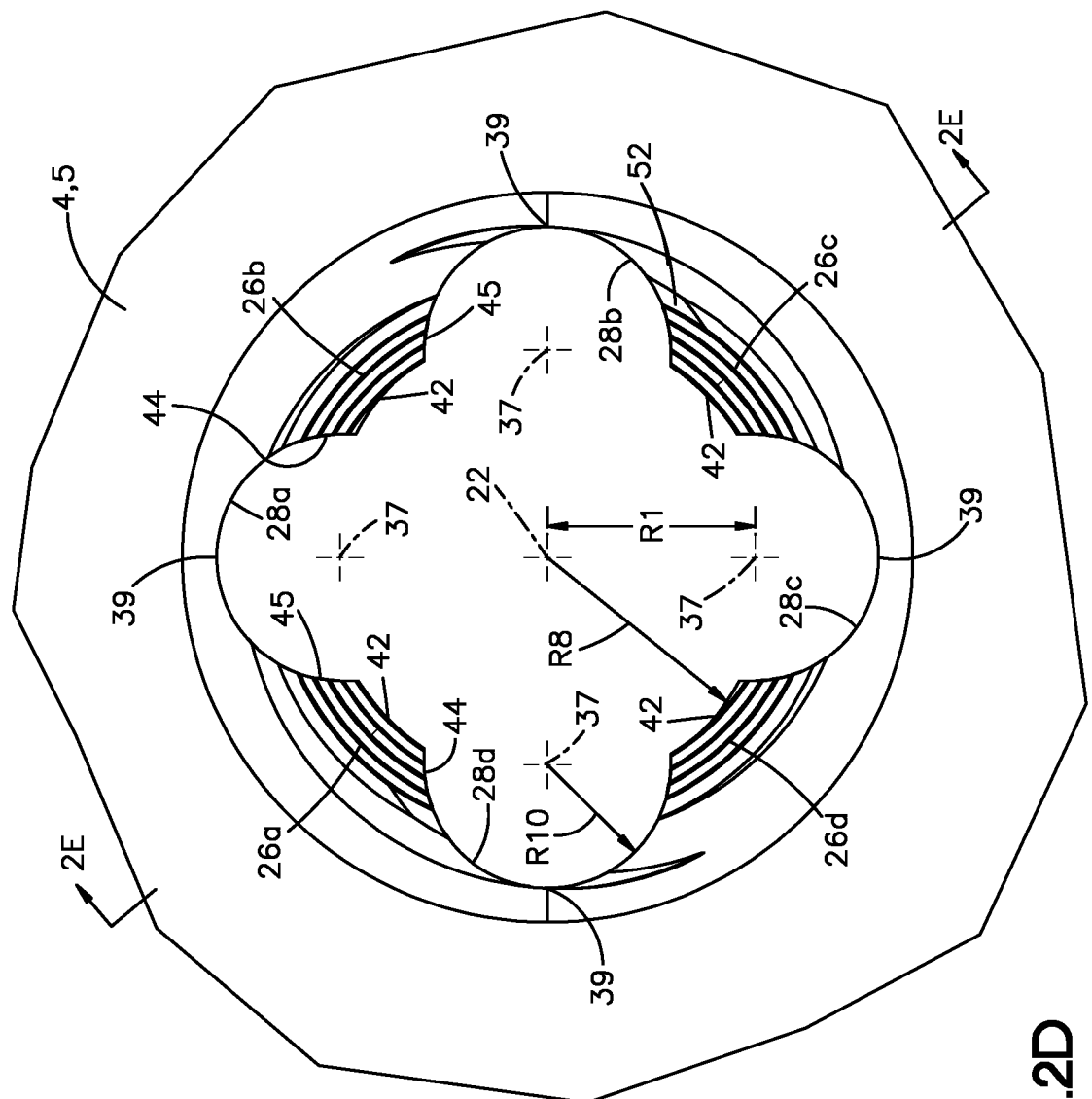
FIG. 2D is a top view of the locking hole of FIG. 2A.

Referring now to FIG. 2D, in an example embodiment, the VA locking hole 6 can include four (4) columns 26 and four (4) recesses 28 evenly spaced about the central hole axis 22. The columns 26 can include a first column 26a, a second column 26b, a third column 26c, and a fourth column 26d evenly spaced about the central hole axis 22. The recesses 28 can include: a first recess 28a located circumferentially between the first and second columns 26a, 26b; a second recess 28b located circumferentially between the second and third columns 26b, 26c; a third recess 28c located circumferentially between the third and fourth columns 26c, 26d, and a fourth recess 28d located circumferentially between the fourth and first columns 26d, 26a. It should be appreciated that the design of the VA locking hole 6 is not limited by the number of columns 26 and recesses 28, as described in more detail below.

Each of the recesses 28a-d can define a central recess axis 37, each of which can be parallel with the central hole axis 22, although other central recess axis 37 orientations are possible. Each central recess axis 37 can also be radially spaced from the central hole axis 22 by radial distance R1. Each recess defines a recess radius R10. As shown, each of the recesses 28a-d has a horizontal profile (i.e., a profile in a reference plane orthogonal to the central hole axis 22) that subsumes about half of a circle. In the illustrated embodiment, each of the recesses 28a-28d is generally shaped as a section of a cylinder. In other embodiments, one or more an up to all of the recesses can have a downward-tapering frusto-conical shape. Other recess shapes are also within the scope of the present disclosure. Each recess 28 defines a radially-outermost region or apex 39, as measured from the central hole axis 22. Each recess apex 39 can extend along a plane, along which the central hole axis 22 also extends.

In the depicted embodiments, the recess apices 39 are parallel with the central hole axis 22. In other embodiments, the recess apices 39 can be oriented at an acute angle relative to the central hole axis 22.

Each column 26 can define a first surface 42 substantially facing the central hole axis 22. The first surface 42 can also be referred to as an "innermost surface" of the column 26. Thus, the first surface 42 defines the crests 56 of the column threads 54. In a horizontal reference plane (such as reference plane M shown in FIG. 2E), the first surface 42 of each column 26 preferably extends arcuately about the central hole axis 22 and defines a shared or common radius R8. The first surface 42 of each column 26 can also extend between a first side 44 and a circumferentially opposed second side 45 of the column 26. The first and second sides 44, 45 of each column 26 can define interfaces between the column 26 and the circumferentially adjacent recesses 28. For example, the first side 44 of the first column 26a can define an interface between the first column 26a and the fourth recess 28d; the second side 45 of the first column 26a can define an interface between the first column 26a and the first recess 28a; the first side 44 of the second column 26b can define an interface between the second column 26b and the first recess 28a; the second side 45 of the second column 26b can define an interface between the second column 26b and the second recess 28b; and so forth along the circumference of the interior surface 24. The first surfaces 42 of the columns 26 can collectively define circumferential segments of a downward-tapering frusto-conical shape, particularly one that defines a central cone axis coincident with the central hole axis 22.

Figure 2E:
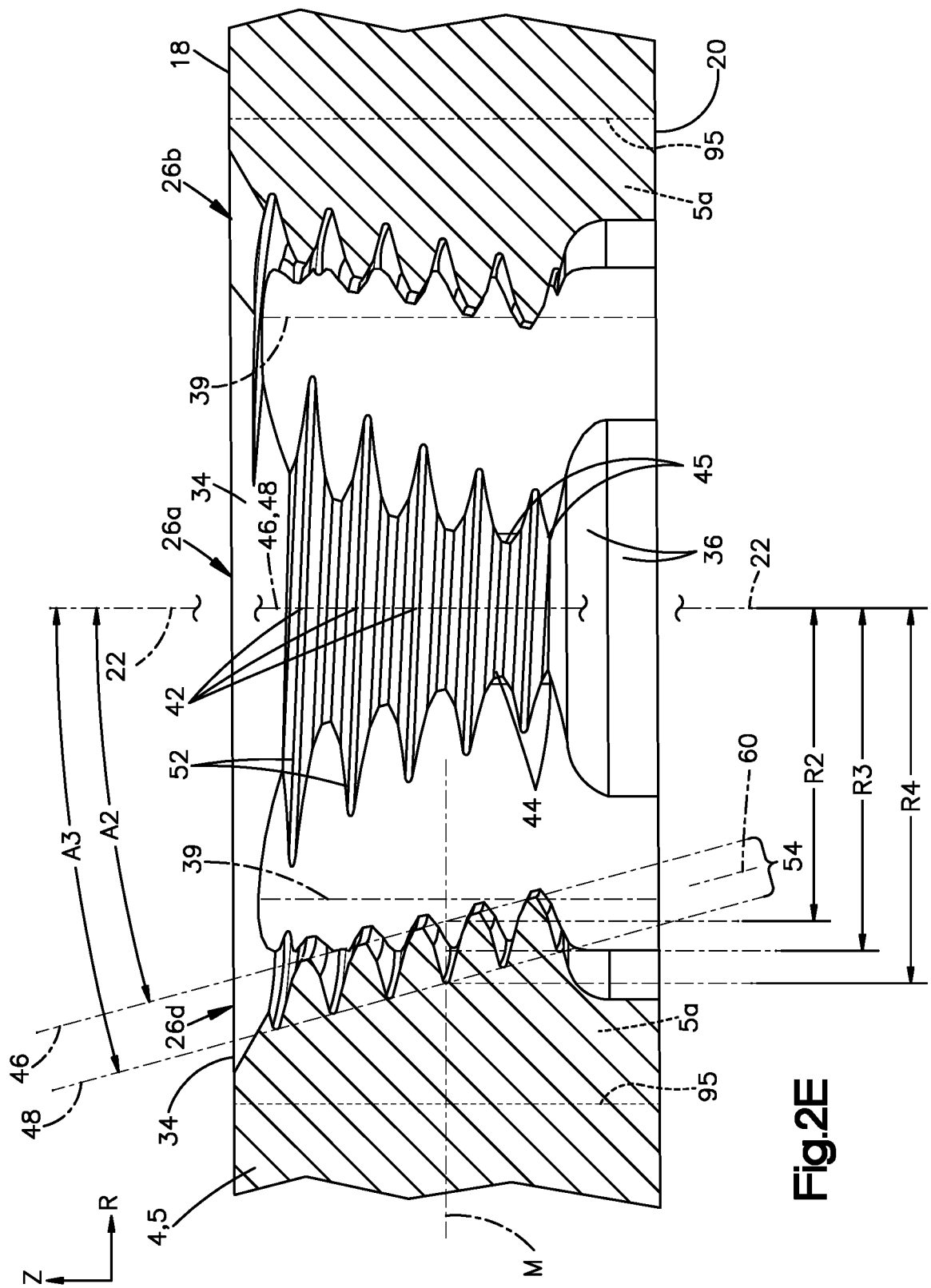
FIG. 2E is a side sectional view of the locking hole taken along section line 2E-2E illustrated in FIG. 2D, showing a threaded locking structure defined by an interior surface of the locking hole, wherein the threaded locking structure is configured to lock with a locking bone screw.

With reference to FIG. 2E, each column 26 can define a crest centerline 46 that is disposed circumferentially equidistantly between the first and second sides 44, 45 of the column 26. In each column 26, the crest centerline 46 extends along the first surfaces 42 and thus intersects the crests 56 of the column threads 54. The crest centerline 46 of each column 26 is coplanar with the central hole axis 22 in a respective axial reference plane. In this manner, each crest centerline 46 also defines a crest trajectory of the column threads 54 in the axial reference plane. Accordingly, the crest centerline 46 can also be referred to as a "crest trajectory axis" 46. Each column 26 can also define a root centerline 48 that is disposed circumferentially equidistantly between the first and second sides 44, 45 of the column 26. In each column 26, the root centerline 48 intersects the roots 58 of the column threads 54. The root centerline 48 of each column 26 is coplanar with the crest centerline 46 and the central hole axis 22 in the respective axial reference plane. In this manner, each root centerline 48 also defines a root trajectory of the column threads 54 in the axial reference plane. Accordingly, the root centerline 48 can also be referred to as a "root trajectory axis" 48. The crest trajectory axis 46 can be oriented at an acute angle A2 relative to the central hole axis 22. The root trajectory axis 48 can also be oriented at an acute angle A3 relative to the central hole axis 22. Acute angles A2 and A3 can be in a range of about 5 degrees to about 30 degrees. In additional embodiments, the angles A2, A3 can be in a range of about 10 degrees to about 20 degrees, and can further be in a range of about 5 degrees to about 30 degree. The crest and root trajectory axes 46, 48 are preferably parallel, as shown. In other embodiments, however, the crest and root trajectory axes 46, 48 of one or more and up to all of the columns 26 can be oriented at an acute angle relative to one another, as described in the '761 Reference. The column threads 54 can also define a thread midline 60, which can lie in the common plane with the crest and root trajectory axes 46, 48 and the central hole axis 22. The thread midline 60 is equidistantly spaced between the crest and root trajectory axes 46, 48.

The crest trajectory axis 46 can be radially spaced from the central hole axis 22 by a distance R2 measured along a reference plane M that is orthogonal to the central hole axis 22 and located at the vertical center of the VA locking hole 6. Thus, the reference plane M can be characterized as the axial "mid-plane" of the VA locking hole 6. The thread midline 60 can be radially spaced from the central hole axis 22 by a distance R3 measured along the hole mid-plane M. The root trajectory axis 48 can be radially spaced from the central hole axis 22 by a distance R4 measured along the hole mid-plane M. Distance R2 can be characterized as the mean crest radius of the column threads 54. Distance R3 can be characterized as the mean radius of the column threads 54. Distance R4 can be characterized as the mean root radius of the column threads 54. It should be appreciated that any of the mean crest radius R2, the mean radius R3, and the mean root radius R4 can optionally be used as a metric for categorizing the size of the hole 6.

Figure 2F:
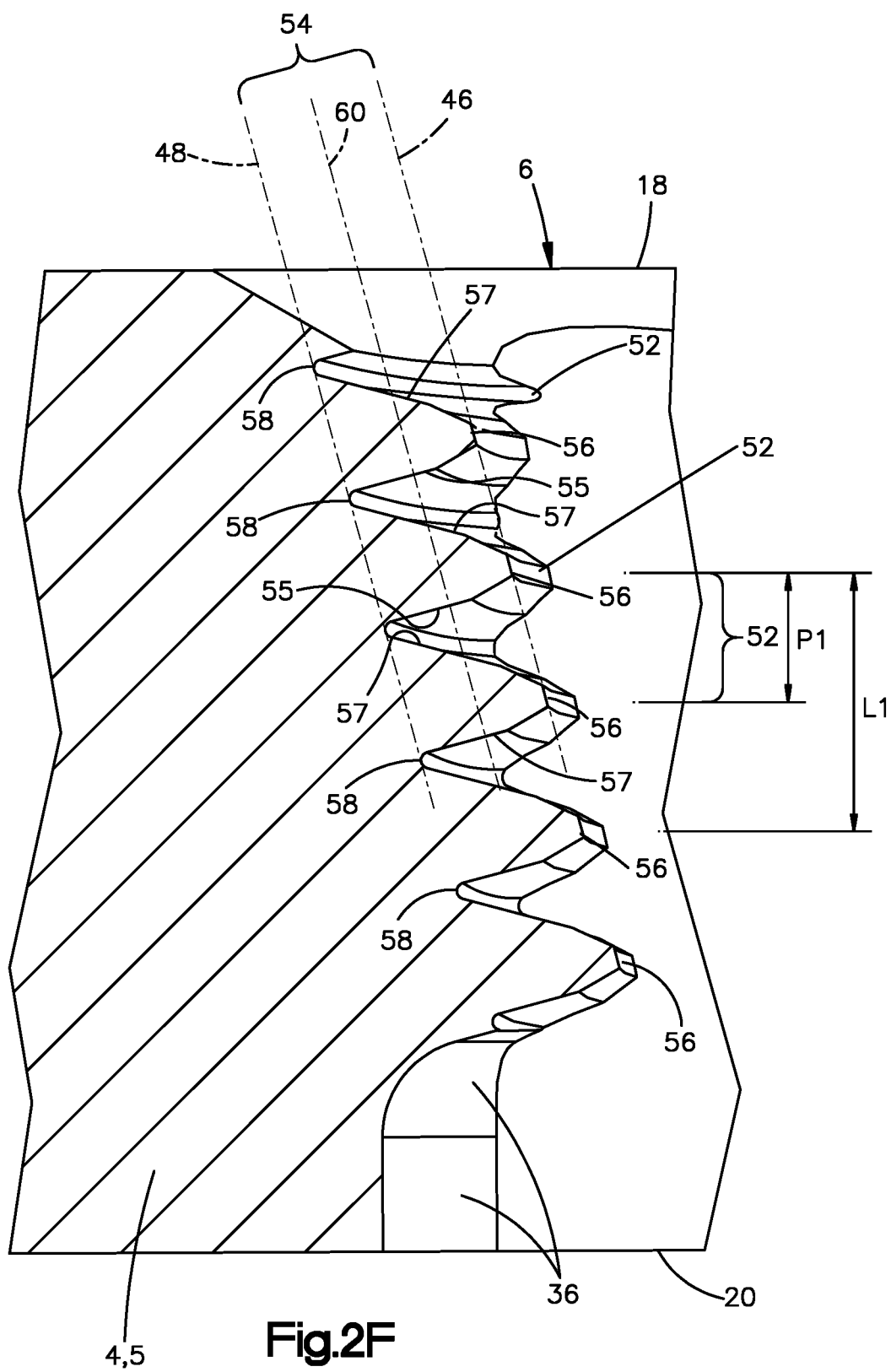
FIG. 2F is an enlarged sectional view of the threaded locking structure shown in FIG. 2E.

Referring now to FIG. 2F, each plate thread segment 52, as an internal thread, can be axially centered at the root 58, and includes the upper flank 55 extending from the root 58 to the axially upward crest 56, and also includes the lower flank 57 extending from the root 58 to the axially lower crest 56. Each plate thread segment 52 is configured to intermesh with (i.e., at least partially house) at least one associated thread segment of the screw head threads 29, as described in more detail below. The plate threads 9 define a thread pitch P1 that extends between axially adjacent crests 56 along the axial direction. The plate threads 9 also define a thread lead L1, which can also be defined at the crests 56. In embodiments where the plate threads 9 are double-lead threads, such as those depicted, the thread pitch P1 of the column threads 54 can be in a range of about 0.15 mm to about 0.6 mm and preferably about 0.4 mm, and the thread lead L1 can be in a range of about 0.3 mm to about 1.2 mm and preferably about 0.8 mm.

Figure 2G:
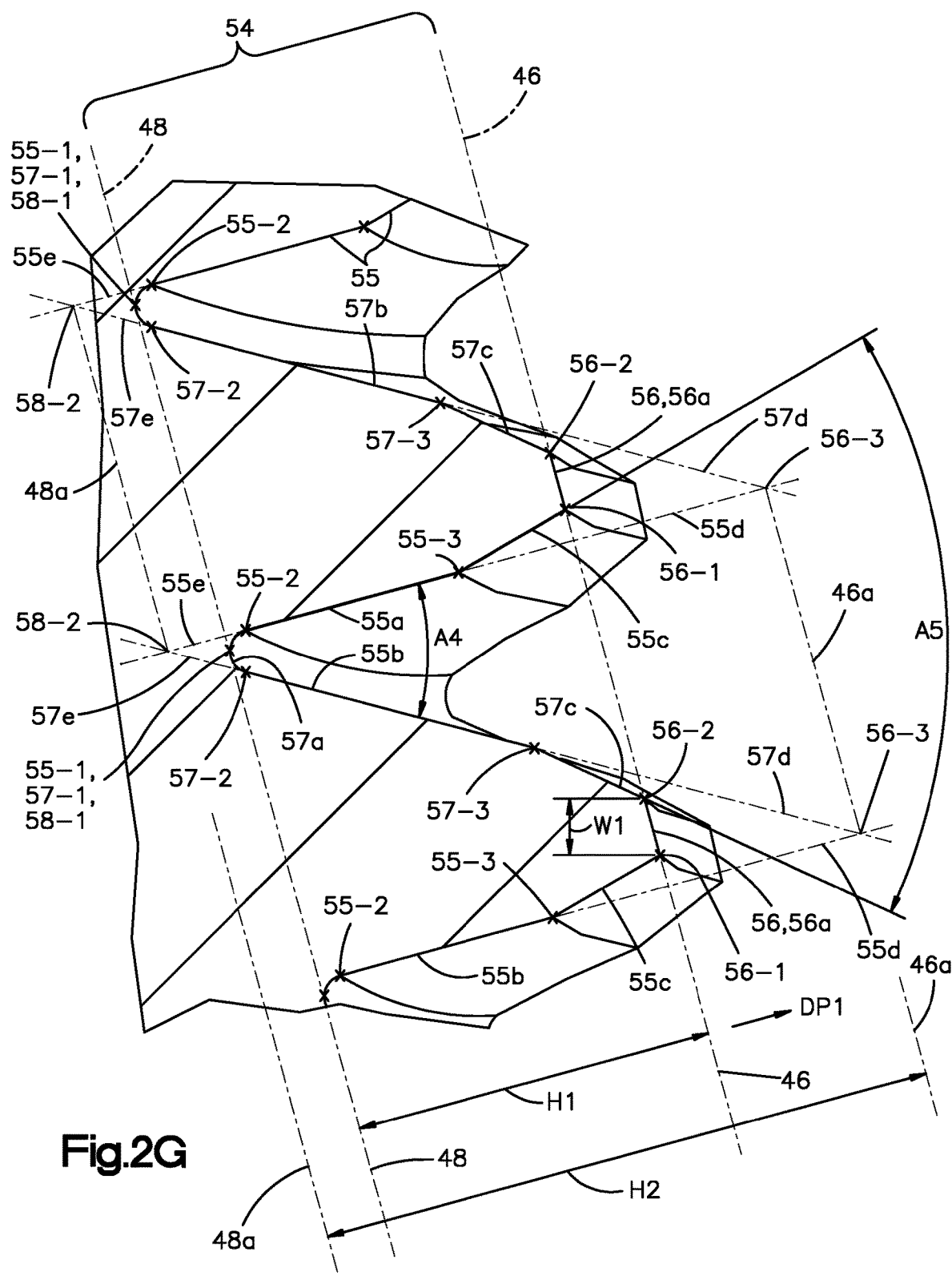
FIG. 2G is a further enlarged section view of a portion of the threaded locking structure shown in FIG. 2F.

Referring now to FIG. 2G, the cross-sectional profiles (i.e., thread-forms) of the plate threads 9 in the axial reference plane will now be described. These cross-sectional profiles can also be referred to herein simply as "thread profiles". In the illustrated embodiment, this reference plane also contains the root trajectory axis 48. The thread profiles of the plate threads 9 are substantially similar in each of the respective axial reference planes of the various thread columns 26. As described above, these thread profiles, and the edge geometries thereof, are configured to be complimentary with those of the plate head threads 29 to provide favorable mating engagement therebetween, such as for controlling thread deformation of, and/or reducing undesirable mechanical interference between, the plate threads 9 and the screw head threads 29.

The first and second flanks 55, 57 are offset from one another at an angle A4, which defines the thread angle of the plate threads 9. Accordingly, angle A4 can also be referred to as "thread angle" A4 of the plate threads 9 or the "plate thread angle" A4. In the illustrated embodiment, the crests 56 of the plate thread segments 52 are truncated for reducing undesirable mechanical interference with the screw head threads 29. Additionally, the first and second flanks 55, 57 can be offset from one another at a plurality of angles. For example, in the illustrated embodiment, upper and lower flanks 55, 57 of the plate thread segments 52 are also truncated adjacent the crests 56 in a manner providing the plate thread segments 52 with a second thread angle A5 adjacent the crests 56. The plate threads 9 of such an embodiment can be referred to as "dual-angle" threads. It should be appreciated that the flanks 55, 57 of the plate thread segments 52 can define yet additional thread angles, such as a third thread angle, a fourth thread angle, etc. In such multi-angle embodiments, including dual-angle embodiments, thread angle A4 can be referred to as a "first thread angle" A4. In yet further embodiments, the flanks 55, 57 (or at least portions thereof) can have arcuate profiles, which can theoretically define an infinite number of thread angles. The particular edge geometries of the thread profiles defined by the truncated crests and truncated flanks 55, 57 are described in more detail below.

In each plate thread segment 52, the root 58 defines a root profile, the crests 56 define crest profiles, and the upper and lower flanks 55, 57 define respective upper and lower flank profiles. In the illustrated embodiment, and with reference to a radially inward direction, the profile of the upper flank 55 includes:
a) a first upper flank portion 55*a* that extends from a first upper flank reference point 55-1 to a second upper flank reference point 55-2;
b) a second or "primary" upper flank portion 55*b* that extends along a consistent geometry from the second upper flank reference point 55-2 to a third upper flank reference point 55-3; and
c) a third upper flank portion 55*c* that extends from the third upper flank reference point 55-3 to a lower crest reference point 56-1.

Similarly, in the illustrated embodiment, and with reference to the radially inward direction, the profile of the lower flank 57 includes:
a) a first lower flank portion 57*a* that extends from a first lower flank reference point 57-1 to a second lower flank reference point 57-2;
b) a second or primary lower flank portion 57*b* that extends along a consistent geometry from the second lower flank reference point 57-2 to a third lower flank reference point 57-3; and
c) a third lower flank portion 57*c* that extends from the third lower flank reference point 57-3 to an upper crest reference point 56-2.

The first upper and lower flank portions 55*a*, 57*a* are coincident with each other and with a root reference point 58-1, which is located at the root 58 (i.e., the location of the thread segment 52 spaced furthest from the crest trajectory axis 46). Additionally, the first upper and lower flank portions 55*a*, 55*b* can each define a relief surface extending from the root 58. As shown, the first upper and lower flank portion 55*a*, 57*a* can each be arcuate and can define a shared or common relief radius R5, which is configured to reduce stress concentrations at the root 58. Thus, the first upper and lower flank portion 55*a*, 57*a* can be referred to as respective "root relief" portions 55*a*, 57*a* of the upper and lower flanks 55, 57. Because the root relief portions 55*a*, 57*a* of the illustrated embodiment have a common boundary at the first root reference point 58-1, the root 58 profile of each thread segment 52 substantially consists of a single point in the axial reference plane. In other embodiments, however, the root 58 can define an elongated root profile, which can extend linearly between the first upper and lower flank reference points 55-1, 57-1 along the root trajectory axis 48 (as described in more detail below with reference to the embodiment shown in FIGS. 5B and 5C).

The primary upper and lower flank portions 55*b*, 57*b* each extend along a consistent geometry in the axial reference plane. As used herein, the term "consistent geometry" means a line, a regular curve, or a portion of a non-regular curve which portion does not include an inflection and does not backtrack on itself. Non-limiting examples of such curves having a consistent geometry include an involute curve, as more fully described in the '047 Reference, and a curve having a constant, relatively large radius. In the illustrated embodiment, the primary flank portions 55*b*, 57*b* extend linearly and define the first thread angle A4. Additionally, the third upper and lower flank portions 55*c*, 57*c* of the illustrated embodiment define the second thread angle A5 therebetween and are offset from the respective primary flank portions 55*b*, 57*b*. The first thread angle A4 of the plate can be in a range of about 28 degrees to about 32 degrees, and can also be in a range of about 20 degrees to about 40 degrees, and can further be in a range of about 15 degrees to about 50 degrees. The second thread angle A5 of the plate can be in a range of about 53 degrees to about 57 degrees, and can also be in a range of about 45 degrees to about 65 degrees, and can further be in a range of about 40 degrees to about 75 degrees. In other embodiments, the primary flank portions 55*b*, 57*b* and the respective third upper and lower flank portions 55*c*, 57*c* of any and up to each of the flank profiles need not have a common boundary at the third lower flank reference point 57-3. For example, such flank profiles can include a transition portion, which can be arcuate, extending between the primary flank portions 55*b*, 57*b* and the respective third upper and lower flank portions 55*c*, 57*c*. In such embodiments, it should be appreciated that the third upper and lower flank reference points 55-3, 57-3 continue to define radially inward ends of the primary flank portions 55*b*, 57*b*.

Furthermore, the thread profiles of the column threads 54 include crest profiles 56*a* that are truncated. In the illustrated embodiment, the crest profile 56*a* extends linearly from the lower crest reference point 56-1 to the upper crest reference point 56-2 along the crest trajectory axis 46, which is also linear. This linear crest profile 56*a* is configured to further reduce stress concentrations at the crest 56. Additionally, each crest profile 56*a* can define a crest width W1, as measured between the upper and lower crest reference points 56-1, 56-2 along the axial plate direction. Additionally, it should be appreciated that the third upper and lower flank portions 55*c*, 57*c*, which can be characterized as chamfers or bevels, can effectively define relief surfaces for the crest 56, which relief surfaces are configured to further reduce stress concentrations at the crest 56. Thus, the third upper and lower flank portion 55*c*, 57*c* can be referred to as respective "crest relief" portions of the flank 55, 57 profiles.

It should be appreciated that the foregoing geometries of the plate thread profiles are provided as examples, and that other profile geometries are within the scope of the present disclosure. For example, the crest profile 56*a* of one or more and up to all of the thread segments 52 in the column 26 can optionally be rounded, radiused, chamfered, and/or beveled, with the crest 56 itself located at the apex of the crest profile 56*a*. Moreover, the root relief portions 55*a*, 57*a* of the flanks 55, 57 can be linear and can extend to the root 58.

The column threads 54 define a thread height H1 measured from the crests 56 to the roots 58 along a direction DP1 that is perpendicular to the crest trajectory axis 46. In particular, the thread height H1 of any of the plate thread segments 52 can be measured from the crest trajectory axis 46 to the root 58 of the respective thread segment 52 along direction DP1. Alternatively or additionally, the thread height H1 of any of the plate thread segments 52 can be measured from the crest 56 to the root trajectory axis 48 along direction DP1. The thread height H1 of the plate column threads 54 can be in a range of about 0.40 mm to about 0.44 mm, and can also be in a range of about 0.32 mm to about 0.48 mm, and can further be in a range of about 0.20 mm to about 0.55 mm. It is to be appreciated that the thread height H1 of the plate thread segments 52 can be constant along the crests 56 of the column 26.

With continued reference to FIG. 2G, it should be appreciated that the thread profiles of the column threads 54 described above deviate from a reference cross-sectional thread profile (i.e., thread-form) that is V-shaped in the axial reference plane, such as the standardized reference thread-forms of the Unified Thread Standard (UTS) and the International Organization for Standardization (ISO). The reference cross-sectional thread profile is also referred to herein as the "reference profile" of the column threads 54. The deviation of the thread profiles from the reference profiles of the column threads 54 cause the actual thread height H1 to be less than a theoretical maximum thread height H2 defined by the reference profiles. This theoretical maximum thread height H2 can also be referred to herein as the "reference height" H2 of the column threads 54. The crests 56 being truncated and/or relieved and the roots 58 being relieved collectively (and each individually) provides such deviations from the reference profile. Additionally, multi-angle flanks 55, 57 and/or or arcuate flank portions also provide deviations from the reference cross-sectional thread profile. The reference height H2 of the column threads 54 is measured, in the axial reference plane, along direction DP1 from a root reference axis 48a to a crest reference axis 46a. The crest reference axis 46a intersects crest reference points 56-3 defined at the apices of the reference profile on a first side thereof. Similarly, the root reference axis 48a intersects root reference points 58-2 defined at apices of the reference profile on a second side thereof opposite the first side.

The reference profile is defined by the actual thread profile of the column threads 54. For example, the reference profile has a thread pitch and thread lead equivalent to those of the column threads 54. Additionally, the reference profile is coincident with the thread profile at least at one recurring location of each thread segment 52 in the axial reference plane. For example, as shown in FIG. 2G, the reference profile can be coincident with each of the upper and lower flanks 55, 57 at least at the second reference points 55-2, 57-2 thereof, and also at another location along the linear primary flank portions 55b, 57b, including at the third reference points 55-3, 57-3 thereof. Thus, for primary flank portions 55b, 57b that are linear, as in the embodiment illustrated in FIG. 2G, each crest reference point 56-3 can also be defined as the intersection of: (1) a projection 55d of the respective primary upper flank portion 55b, which projection 55d extends from the third upper flank reference point 55-3 and along the consistent linear geometry of the primary upper flank portion 55b toward the central hole axis 22, and (2) a projection 57d of the respective primary lower flank portion 57b the adjacent, axially upward thread segment 52, which projection 57d extends from the third lower flank reference point 57-3 and along the consistent linear geometry of the primary lower flank portion 57b toward the central hole axis 22. In such embodiments, the crest reference points 56-3 of the column threads 54 represent the theoretical crest locations at which these linear primary upper and lower flank portions 55b, 57b would converge if they extended uninterrupted (i.e., in an un-truncated fashion) toward the central hole axis 22.

Similarly, in embodiments where the primary flank portions 55b, 57b are linear, each root reference point 58-2 can also be defined as the intersection of: (1) a projection 55e of the respective primary upper flank portion 55b, which projection 55e extends from the second upper flank reference point 55-2 and along the consistent linear geometry of the primary upper flank portion 55b away from the central hole axis 22, and (2) a projection 57e of the respective primary lower flank portion 57b the adjacent, axially downward thread segment 52, which projection 57e extends from the second lower flank reference point 57-2 and along the consistent linear geometry of the primary lower flank portion 57b away from the central hole axis 22. In such embodiments, the root reference points 58-2 of the column threads 54 represent the theoretical root locations at which these linear primary upper and lower flank portions 55b, 57b would converge if they extended uninterrupted (i.e., in an un-relieved fashion) away from the central hole axis 22. Additionally, in view of the foregoing, it is to be appreciated that the reference height H2 represents the theoretical maximum thread height if the primary upper and lower flank portions 55b, 57b of the column threads 54 extended linearly from un-truncated or un-relieved crests (i.e., at the crest reference points 56-3) to un-relieved, intersecting roots (i.e., at the root reference points 58-2).

Figure 2H:
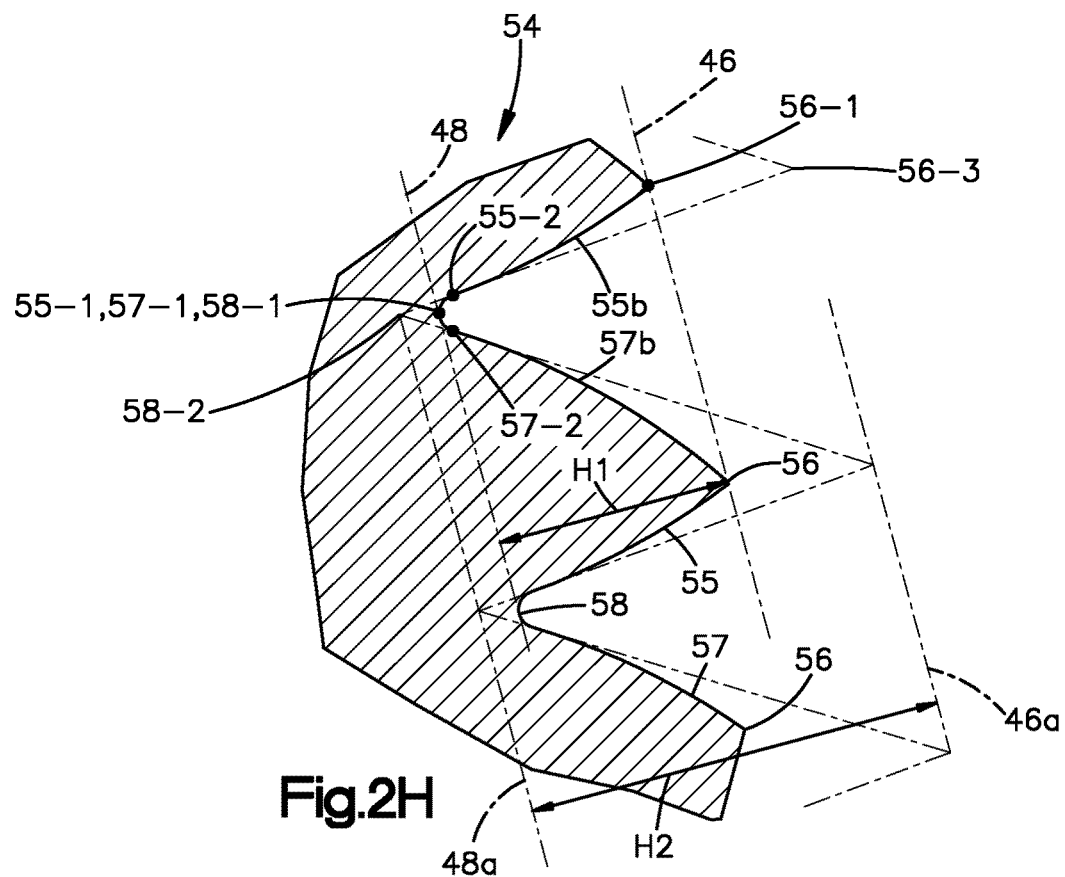
FIG. 2H is an enlarged sectional view of a portion of the threaded locking structure having an alternative geometry to that shown in FIG. 2G.

Referring now to FIG. 2H, an example embodiment of the column threads 54 is shown, in which the column threads 54 have arcuate flank profiles that deviate from the reference profile to cause the thread height H1 to be less than the reference height H2. In this example embodiment, the consistent geometry of the primary portions 55b, 57b of the upper and lower flanks 55, 57 is an involute curve, which extends radially inward from the respective second flank reference point 55-2, 57-2. In this particular example, the primary portions 55b, 57b extend all the way to the crest reference point 56-1 located at the crest 56. It should be appreciated that the crest 56 can optionally be further relieved and/or truncated, such as by being chamfered, beveled, and/or rounded, by way of non-limiting examples. The reference profile can be coincident with each of the upper and lower flanks 55, 57 at least at the second flank reference points 55-2, 57-2 thereof, that is, at the location at which the primary flank portions 55b, 57b intersect the root relief portions 55a, 57a. It should be appreciated that, when the root relief portions 55a, 57b are arcuate (including along an involute curve, as shown), the lines of the V-shaped reference profile can be defined as extending tangentially from the root relief portions 55a, 57b at the second reference points 55-2, 57-2. As described above, the lines of the reference profile extend from crest reference points 56-3 to root reference points 58-2.

Figure 2I:
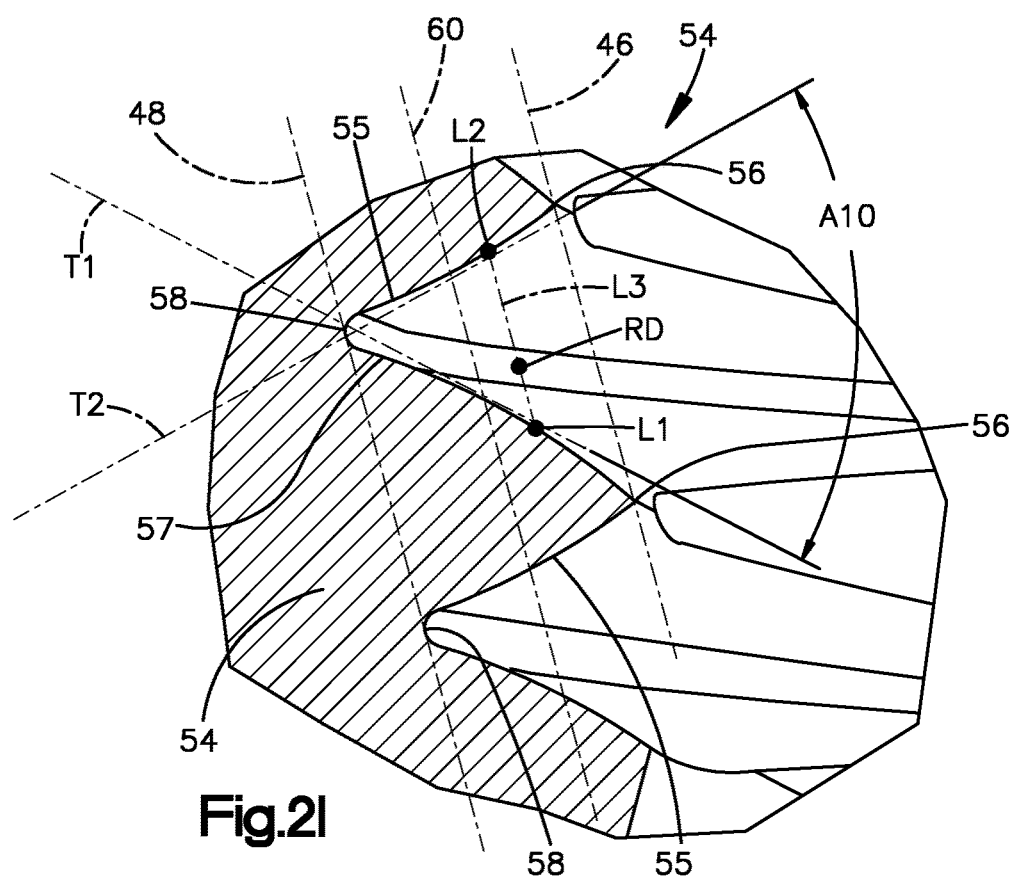
FIG. 2I is another view of the enlarged sectional view of FIG. 2H.

Referring now to FIG. 2I, the curved profile of the flanks 55, 57 defines a varying thread angle A10. At any radial location RD of the column threads 54, the varying thread angle A10 can be defined as the angle between a pair of tangent lines T1, T2 intersecting the primary flank portions 55b, 57b at respective locations L10, L20 along a reference line L30 parallel with the thread midline 60 and coincident with the radial location RD. In such embodiments, the varying thread angle A10 can vary within any of the ranged described above with reference to angle A4.

Figure 3A:
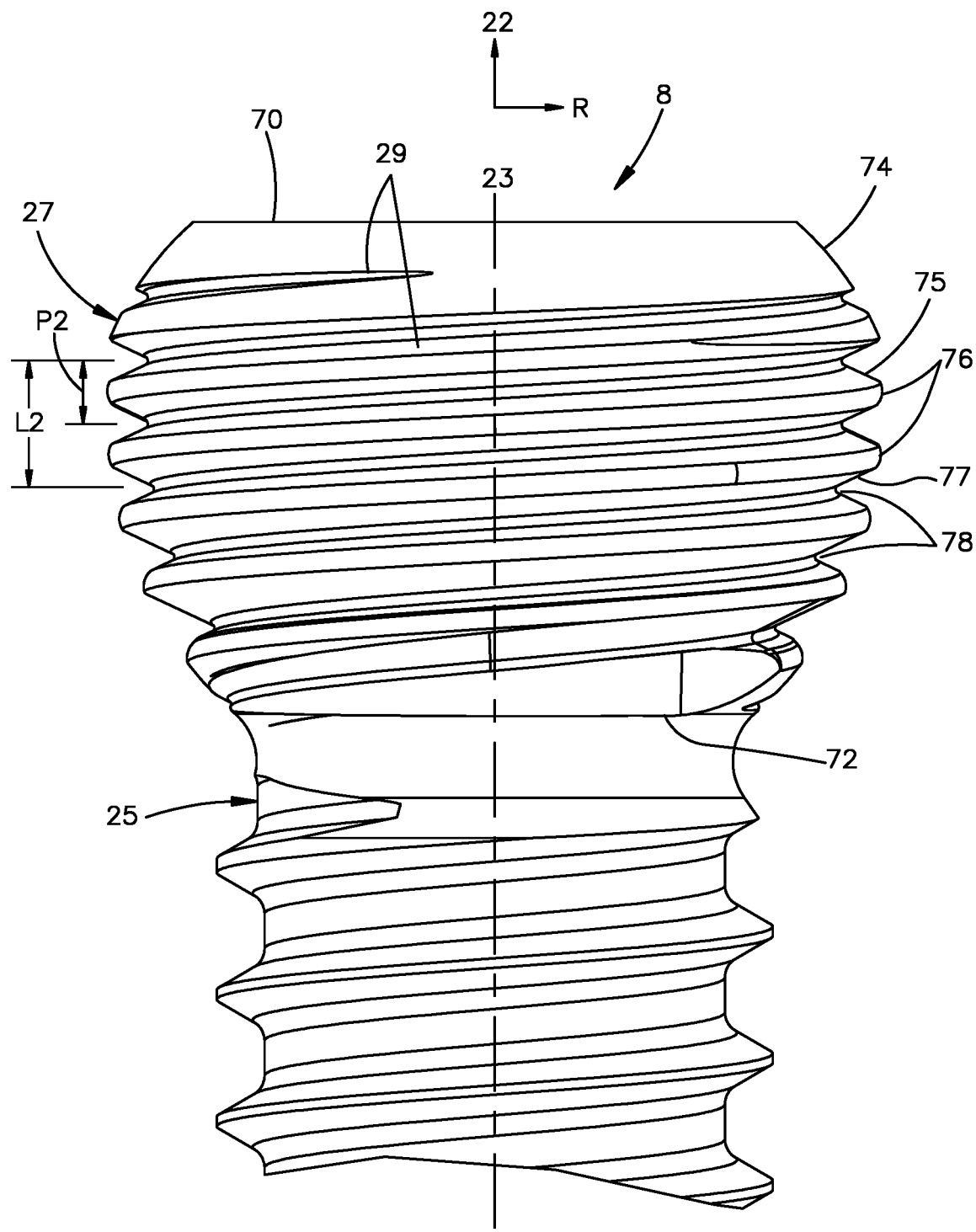
FIG. 3A is a side view of a head of a variable-angle (VA) locking screw configured to be locked to the bone plate of FIG. 1A within one of the locking holes.

Referring now to FIG. 3A, the head 27 of the VA locking screw 8 defines a proximal end 70 and a distal end 72 spaced from the proximal end 70 along an axial screw direction Z2 oriented along the central screw axis 23. The head 27 also defines an outer surface 74 that extends from the proximal end 70 to the distal end 72 and defines the external screw head threads 29. In the illustrated embodiment, the external screw head threads 29 extend substantially from the proximal end 70 to substantially the distal end 72 of the head 27 along one or more thread paths, which can be helical. The external screw head threads 29 define crests 76 spaced radially outwardly from roots 78 with respect to the central screw axis 23. The screw head threads 29 also define upper flanks 75 and lower flanks 77 that extend from the crests 76 to respective axially upper and lower roots 78.

The screw head threads 29 can define a thread pitch P2 and a thread lead L2, which can be measured with respect to the roots 78. As shown, the one or more thread paths can include a pair of non-intersecting thread paths, such as double-lead threads, in which the threads 29 define a thread lead L2 that is equivalent to twice the thread pitch P2. However, in other embodiments, the one or more thread paths of the screw head threads 29 can include a single thread path (i.e., single-lead) or three or more thread paths (e.g., triple-lead, etc.). The one or more thread paths of the plate head threads 29 are configured to be complimentary with the one or more thread paths of the plate threads 9. It should be appreciated, however, that the screw head threads 29 and the plate threads 9 need not have the same number of thread paths. By way of a non-limiting example, one of the plate threads 9 and the screw head threads 29 can be double-lead threads defining a thread pitch, while the other of the plate threads 9 and screw head threads 29 can be single-lead threads having a thread lead that is substantially equivalent to the foregoing thread pitch. Other variations in the thread paths of the plate threads 9 and the screw threads 29 are also within the scope of the present disclosure.

Referring now to FIG. 3B, in an axial reference plane that extends along the central screw axis 23, the external screw head threads 29 define a crest trajectory axis 86 that intersects the crests 76 and a root trajectory axis 88 that intersects the roots 78. As shown, the crest trajectory axis 86 and the root trajectory axis 88 can define arcuate, convex shapes, which is advantageous for angulated locking with the plate threads 9. In additional embodiments, the crest and root trajectory axes 86, 88 can be generally spherical. As used herein, the term "spherical" its derivatives means at least a portion of a sphere or at least a portion of a spheroid, including such portions of a prolate spheroid and/or an oblate spheroid, by way of non-limiting examples, and also encompasses substantial approximations of such portions of a sphere and/or spheroid. It should be appreciated, however, that other crest and root trajectory axis 86, 88 geometries are within the scope of the present disclosure, including those described more fully in the '284 Reference.

The external screw head threads 29 can be characterized as defining a sequence of helically-adjacent screw head thread segments 73, which can extend continuously or discontinuously along the one or more thread paths. As depicted, the screw head threads 29 can define thread segments 73 that are axially adjacent. Because the screw head threads 29 are external threads, each thread segment 73 thereof can be axially centered at the crest 76, and includes the upper flank 75 ascending from the crest 76 to the axially upward root 78, and also includes the lower flank 77 descending from the crest 76 to the axially lower root 78. Accordingly, each thread segment 73 of the screw head threads 29 is configured to intermesh with (i.e., at least partially reside within) at least one associated thread segment 52 of the plate threads 9. The upper and lower flanks 55, 57 of axially adjacent thread segments 73 are offset from one another at an angle A6, which defines the thread angle of the screw head threads 29. Thus, angle A6 can also be referred to the "head thread angle" A6.

Figure 3C:
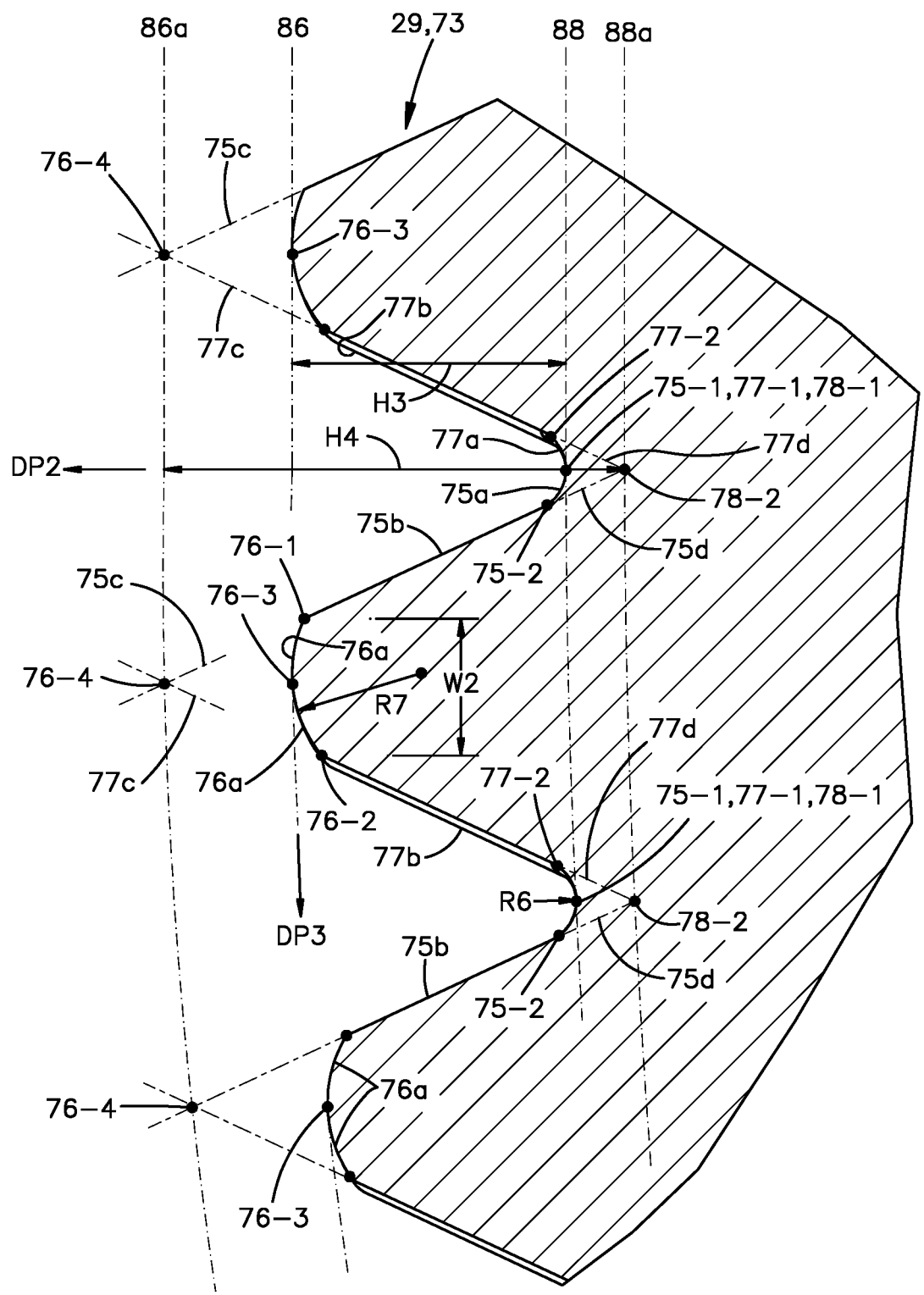
FIG. 3C is an enlarged sectional side view of a portion of the VA locking screw illustrated in FIG. 3B.

Referring now to FIG. 3C, the thread profiles (i.e., threadforms) of the screw head threads 29 will now be described, as defined within the axial reference plane that contains (and is thus oriented along) the central screw axis 23.

As above, the crests 76 define crest profiles; the roots 78 define root profiles; and the upper and lower flanks 75, 77 define respective upper and lower flank profiles. In the illustrated embodiment, and with reference to a radially outward direction away from the central screw axis 23, the profile of the upper flank 75 includes:
  a) a first upper flank portion 75a (also referred to as a "root relief portion") that extends from a first upper flank reference point 75-1 to a second upper flank reference point 75-2; and
  b) a second or "primary" upper flank portion 75b that extends along a consistent geometry from the second upper flank reference point 75-2 to an upper crest reference point 76-1.

Similarly, in the illustrated embodiment, and with reference to the radially inward direction, the profile of the lower flank 77 includes:
  a) a first lower flank portion 77a (also referred to as a "root relief portion") that extends from a first lower flank reference point 77-1 to a second lower flank reference point 77-2; and
  b) a second or primary lower flank portion 77b that extends along a consistent geometry from the second lower flank reference point 77-2 to a lower crest reference point 76-2.

As above, the root relief portions 75a, 77a are configured for reducing stress concentrations at the roots 78 of the screw head threads 29. In the illustrated embodiment, the lower root relief portion 77a of a thread segment 73 is coincident with the upper root relief portion 75a of the axially lower head thread segment 73. In particular, reference points 77-1 and 75-1 are coincident with each other and with a root reference point 78-1, which is coincident with the root 78 (i.e., the nadir of the thread segment 73). As shown, these contiguous root relief portions 77a, 75a can each be arcuate and can define a common relief radius R6, which can be in a range of about 0.03 mm to about 0.05 mm, and can also be in a range of about 0.02 mm to about 0.10 mm, and can further be greater than 0.10 mm (i.e., not less than 0.10 mm), including a relief radius large enough to approximate a linear root profile in the axial reference plane. Accordingly, the first lower and upper flank portions 77a, 77a can be referred to as respective "root relief" portions of the flanks 77, 75. As depicted, the root 78 profile of each head thread segment 73 can consist of a single point 78-1, although in other embodiments the root profile can be elongated, including linearly, in the axial reference plane.

In the illustrated embodiment, the consistent geometries of the primary flank portions 75b, 77b are linear, and define the head thread angle A6, which can be in a range of about 48 degrees to about 52 degrees, and can also be in a range of about 40 degrees to about 60 degrees, and can further be in a range of about 25 degrees to about 75 degrees. It should be appreciated that the primary flank portions 75b, 77b can alternatively define consistent geometries that are non-linear, such as curved, including an involute curve, similarly as described above with reference to FIGS. 2H and 2I, or a curve having a constant, relatively large radius.

The head thread segments 73 define crest profiles 76a that extend between the upper and lower crest reference points 76-1, 76-2. The crest profiles 76a can be convex, and are preferably radiused, rounded, chamfered, beveled, or otherwise truncated and/or relieved for reducing stress concentrations along the crest profile 76a. As depicted, the crest profile 76a can define a relief radius R7, which can be in a range of about 0.11 mm to about 0.13 mm, and/or in a range of about 0.07 mm to about 0.15 mm, and/or in a range of about 0.03 mm to about 0.18 mm. In such convex profiles, a crest tip reference point 76-3 is defined at the apex of the crest profile 76a, as measured from the central screw axis 23. The crest trajectory axis 86 intersects each of the crest tip reference points 76-3. Additionally, the crest profiles 76a can define respective crest widths W2, as measured between the upper and lower crest reference points 76-1, 76-2 along a direction DP3 oriented along the crest trajectory axis 86 at the crest tip reference point 76-3. The crest width W2 can be in a range of about 0.11 mm to about 0.15 mm, and/or in a range of about 0.08 mm to about 0.18 mm, and/or in a range of about 0.01 mm to about 0.20 mm. In some embodiments, the crest width W2 is 0.10 mm or greater (i.e., no less than 0.10 mm). It should be appreciated that the foregoing geometries of the crest profiles 76a are provided as non-limiting examples, and that other crest profile geometries are within the scope of the present disclosure, including linear crest profiles 76a.

The screw head threads 74 define a head thread height H3 measured from the crest 76 to the root 78 in the axial reference plane. In particular, the head thread height H3 of any of the head thread segments 73 is measured between the root reference point 78-1 to the crest trajectory axis 86, along a direction DP2 perpendicular to that portion of the crest trajectory axis 86. The head thread height H3 can be in a range of about 0.24 mm to about 0.28 mm, and can also be in a range of about 0.20 mm to about 0.30 mm, and can further be in a range of about 0.12 mm to about 0.34 mm.

Similarly as described above with reference to the plate threads 9, the thread profiles of the screw head threads 29 deviate from a reference cross-sectional thread profile (i.e., "reference profile") that is V-shaped in the axial reference plane. This deviation from the reference profile of the screw head threads 29 causes the actual head thread height H3 to be less than a theoretical maximum head thread height H4 comprising un-truncated and/or un-relieved crests 76 and un-relieved roots 78. This theoretical maximum head thread height H4 can also be referred to herein as the "reference height" H4 of the screw head threads 29. The reference height H4 of the screw head threads 29 is measured, in the axial reference plane, from a root reference axis 88a to a crest reference axis 86a, along direction DP2. The crest reference axis 86a intersects reference points 76-4, which are defined at the apices of the reference profile on a first side thereof. Also similarly, the root reference axis 88a intersects reference points 78-2, which are defined at apices of the reference profile on a second side thereof opposite the first side. The reference height H4 of the screw head threads 29 represents the theoretical maximum head thread height should the primary upper and lower flank portions 75b, 77b extend from a un-truncated crest to an un-relieved root.

As above, the reference profile of the screw head threads 29 is defined by the actual thread profile of the screw head threads 29, and has a thread pitch and thread lead equivalent to those of the screw head threads 29. Additionally, the reference profile is coincident with the thread profile at least at one recurring location of each thread segment 73 in the axial reference plane. For example, as shown in FIG. 3C, the reference profile can be coincident with each of the upper and lower flanks 75, 77 at least at the second flank reference points 75-2, 77-2 thereof, and also at each location along the linear primary flank portions 75b, 77b, including at reference points 76-1 and 76-2. Thus, for linear primary flank portions 75b, 77b: each crest reference point 76-4 can also be defined by intersections of projections 75c, 77c of the upper and lower primary flank portions 75b, 77 along their respective consistent geometries away from the central screw axis 23; and each root reference point 78-2 can also be defined by intersections of projections 75d, 77d of the primary flank portions 75b, 77 along their respective consistent geometries toward the central screw axis 23.

Figure 4A:
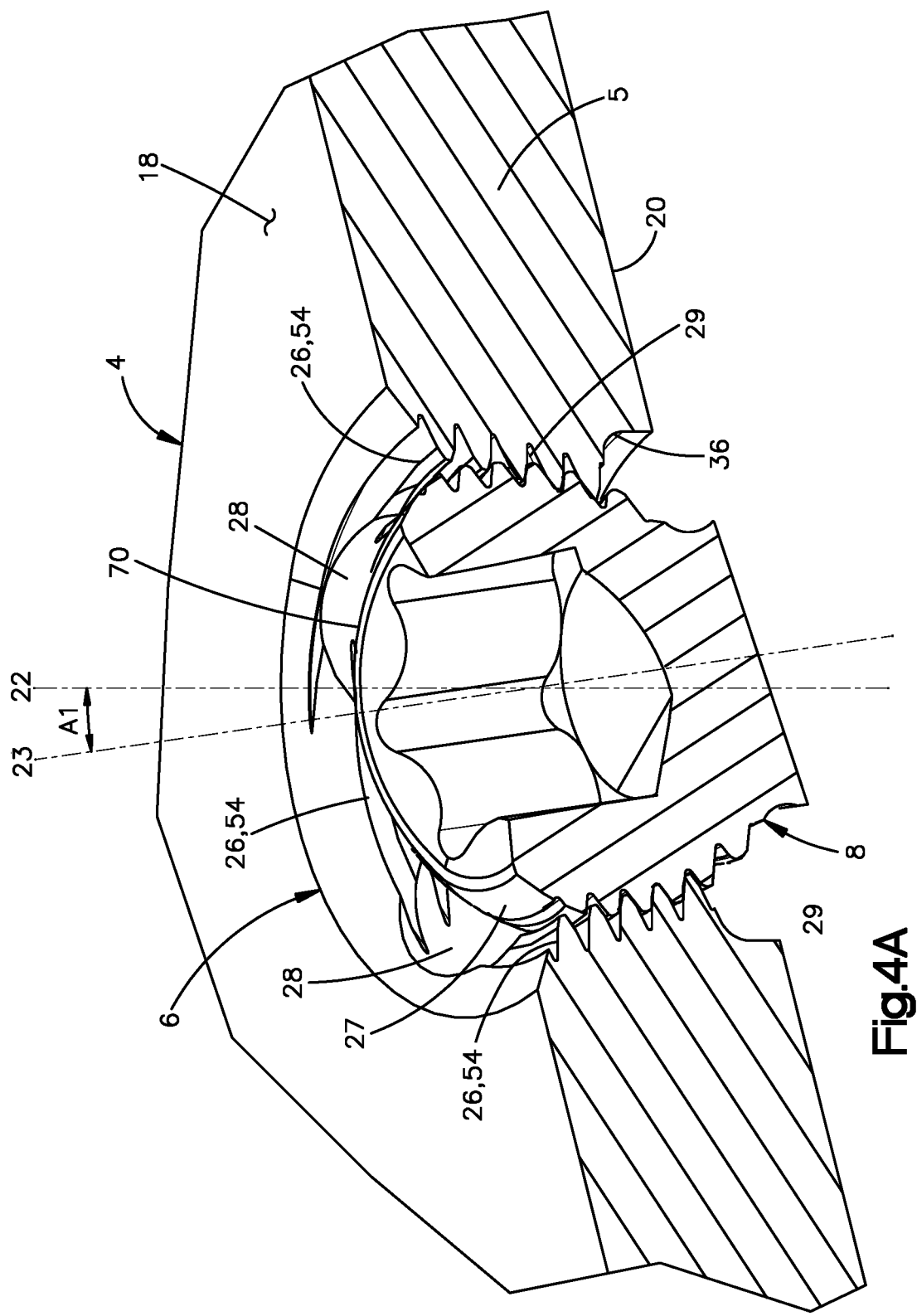
FIG. 4A is a sectional perspective view of the head of the VA locking screw illustrated in FIG. 3A in locking engagement with the locking hole illustrated in FIG. 2A.
Figure 4B:
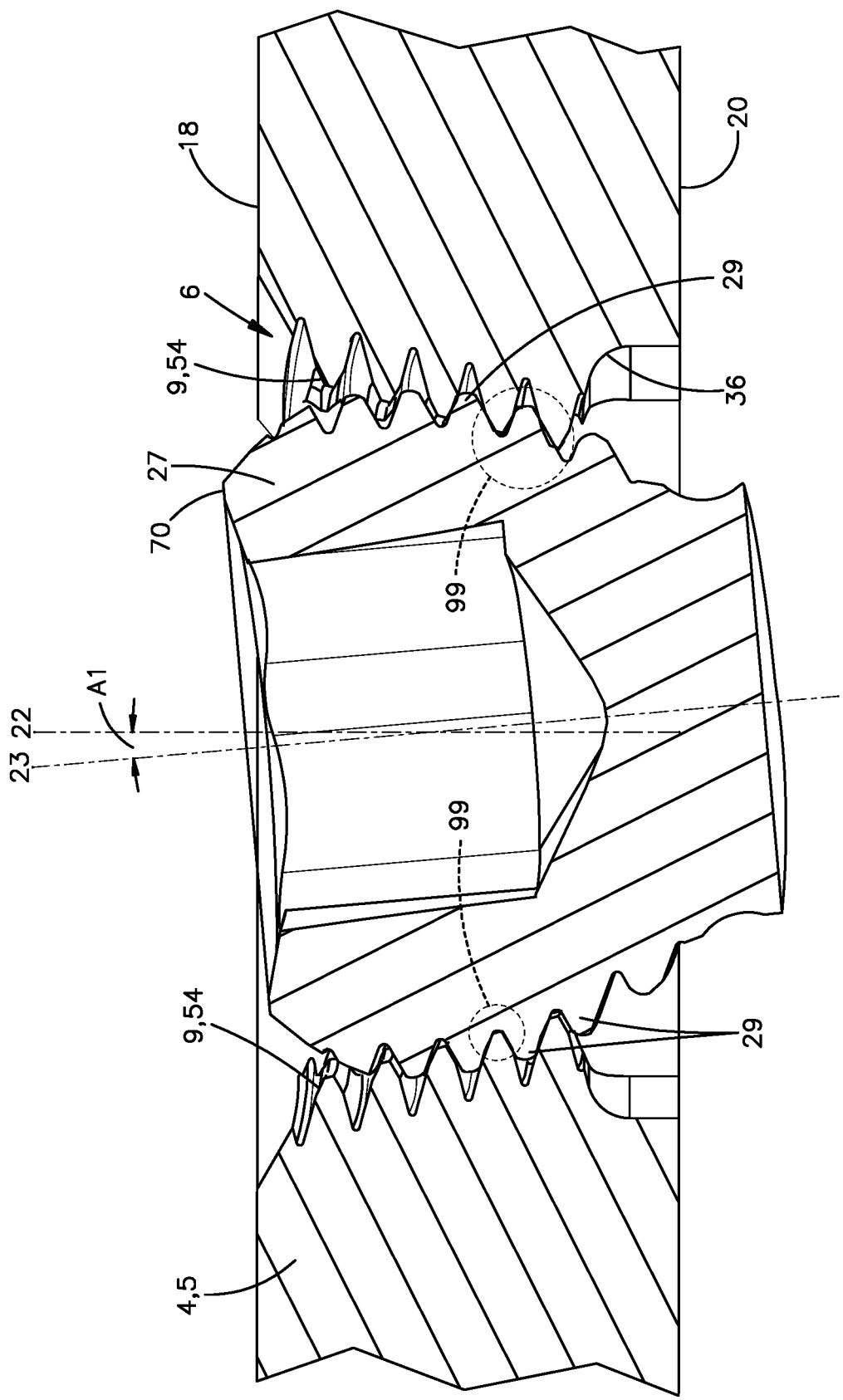
FIG. 4B is a sectional side view of the head of the VA locking screw in locking engagement with the locking hole illustrated in FIG. 4A.

Referring now to FIGS. 4A and 4B, the complimentary thread proportions described above can enhance the mechanical strength of the locked thread interface between the plate threads 9 and the screw head threads 29. For example, the thread profile geometry of the dual-angle column threads 54 can provide an increased form-fit, particularly at angulated screw 9 insertion trajectories, such as that depicted in FIGS. 4A and 4B. Additionally, the axial space between the opposed flank profiles 55a-c, 57a-c provides favorable clearance between the roots 58 of the plate threads 9 and the crests 76 of the screw head threads 29. Such crest-to-root 76-58 clearance is particularly beneficial at angulated insertion trajectories because it prevents or at least reduces undesirable mechanical interference between the head crests 76 and the plate roots 58. Additionally, the rounded crest profiles 76a of the screw head threads 29, particularly those having relatively large relief radii R7, effectively rounds or removes sensitive edges of the screw head threads 29 that could otherwise deleteriously mechanically interfere with plate threads 9.

A further advantage provided by the thread proportions described herein is that a measure of control is provided over the thread deformation at the thread interface. In particular, by interfacing the stronger profile of the screw head thread segments 73 against the more malleable profile of the plate thread segments 52, a vast majority of the thread deformation can be imparted to the plate threads 9. At angulated screw 9 insertion trajectories, such controlled deformation can allow the plate threads 9 to deform so as to effectively re-align to the angulated central screw axis 23. Such controlled deformation also provided enhanced locking with the angulated screw head 27. After form-fit is achieved, further rotational advancement of the VA locking screw 8 with respect to the column threads 54 can commence deforming the one or more column threads 54, preferably at the crests 56, as shown at interference regions 99 in FIG. 4B. This deformation occurs primarily radially outward, although some measure of axial and/or circumferential deformation can occur (mostly when a timing-error is present). Moreover, the radial deformation can include plastic and elastic deformation, which compresses the one or more column threads 54 in a manner exerting a reactive compressive force against the associated screw head threads 29, primarily at the roots 78 thereof, achieving a locking press-fit with the screw head 27. It is to be appreciated that the plate threads 9 are also axially deformable, which allows the plate threads 9 to deform axially downward or upward, such as when the VA locking screw 8 is inserted with timing error.

With respect to the foregoing aims of enhancing the mechanical strength of the locked thread interface and reducing cross-threading, particularly at of the screw head 27 at angulation, and also limiting cross-threading so that is occurs substantially entirely within the plate threads 29 and as an act of plastic and elastic thread deformation, the inventors have identified, through their own extensive testing, particularly effective parameters of the thread proportions discussed above. One such thread proportion parameter for the plate threads 9 and screw head threads 29 is the relationship between the actual thread height H1, H3 versus the reference height H2, H4. For example, the plate threads 9, particularly the column threads 54, define a plate thread height factor ("HF-P"), which is calculated as a ratio of the actual thread height H1 to the reference height H2 of the column threads 54 (i.e., (HF-P)=H1/H2). The plate thread height factor (HF-P) is preferably in a range of about 0.50 to about 0.60, and can also be in a range of about 0.40 to about 0.75, and can further be in a range of about 0.30 to about 1.00. Similarly, the screw head threads 29 define a screw head thread height factor ("HF-S"), which is calculated as a ratio of the actual thread height H3 to the reference height H4 of the screw head threads 29 (i.e., (HF-S)=H3/H4). The screw head thread height factor (HF-S) is preferably in a range of about 0.63 to about 0.67, and can also be in a range of about 0.55 to about 0.75, and can further be in a range of about 0.40 to about 0.90. The screw head thread height factor (HF-S) is preferably combined with a rounded crest profile 76a having a relatively large crest width W2, as well as a relatively large relief radius R7, such as the values of W2 and R7 described above.

Additionally, the plate threads 9 (particularly the column threads 54) and the screw head threads 29 can define a comparative height factor ("CHF"), which is calculated herein as a ratio of the actual thread height H1 of the plate threads 9 to the actual thread height H3 of the screw head threads 29 (i.e., CHF=H1/H3). The comparative height factor (CHF) is preferably in a range of about 1.58 to about 1.62, and can also be in a range of about 1.30 to about 1.90, and can further be in a range of about 1.00 to about 2.00.

In combination with the foregoing values recited for the plate thread height factor (HF-P), the screw head thread height factor (HF-S), and the comparative height factor (CHF), the inventors have discovered through their extensive testing that particularly favorable thread deformation occurs when plate thread angle A4 is in a range from 25 degrees to 35 degrees and the head thread angle A6 is in a range from 45 degrees to 60 degrees, including the multi-angle embodiments where A4 is the first thread angle of the plate threads 9. The inventors have discovered, surprisingly and unexpectedly, that the foregoing combination of parameters can cause most if not substantially all of the thread deformation at the locking interface between the plate threads 9 and screw head threads 29 to occur within the plate threads 9. Stated differently, the inventors have discovered a particular combination of thread parameters that effectively cause the screw head threads 29 to plastically deform the plate threads 9 substantially without being plastically deformed themselves.

It is to be appreciated that the designs of the VA locking holes 6 and the screw head 27, including the thread proportion parameters thereof, can be adjusted while remaining within the scope of the present disclosure. For example, additional embodiment of the VA locking hole 6 will now be described with reference to FIGS. 5A-9D. The VA locking holes 6 of these additional embodiments are generally similar to the VA locking hole 6 described above with reference to the preceding embodiment described above with reference to FIGS. 2A through 2G. Accordingly, like reference numbers from the preceding embodiment will also be used in these additional embodiments. Moreover, it should be appreciated that, for the sake of brevity, the following disclosure will focus primarily on the differences between the VA locking holes 6 of these additional embodiment and the preceding embodiment.

Figure 5A:
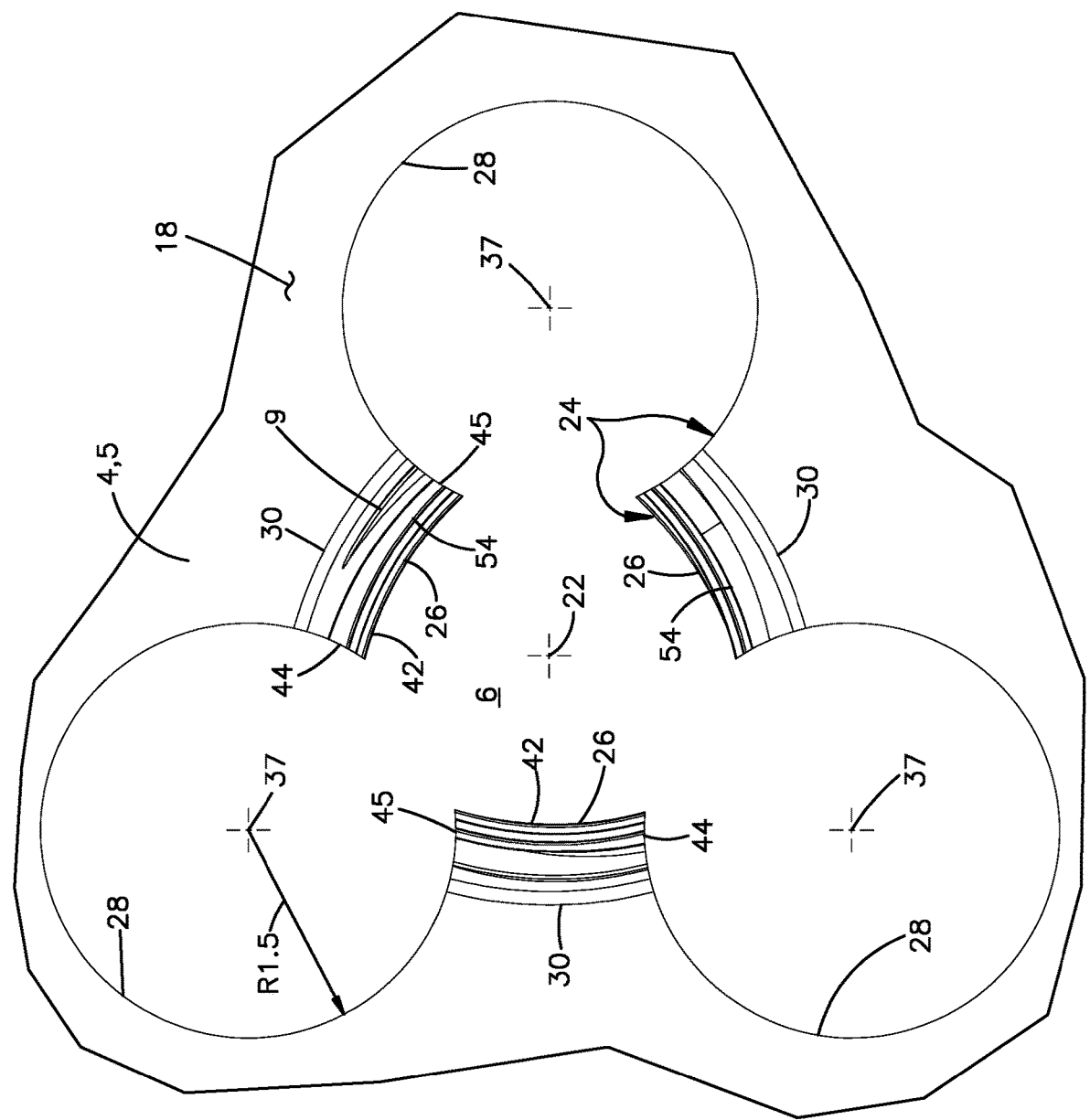
FIG. 5A is a top view of another locking hole, which has a threaded locking structure defined by an interior surface of the locking hole, according to another embodiment of the present disclosure.
Figure 5B:
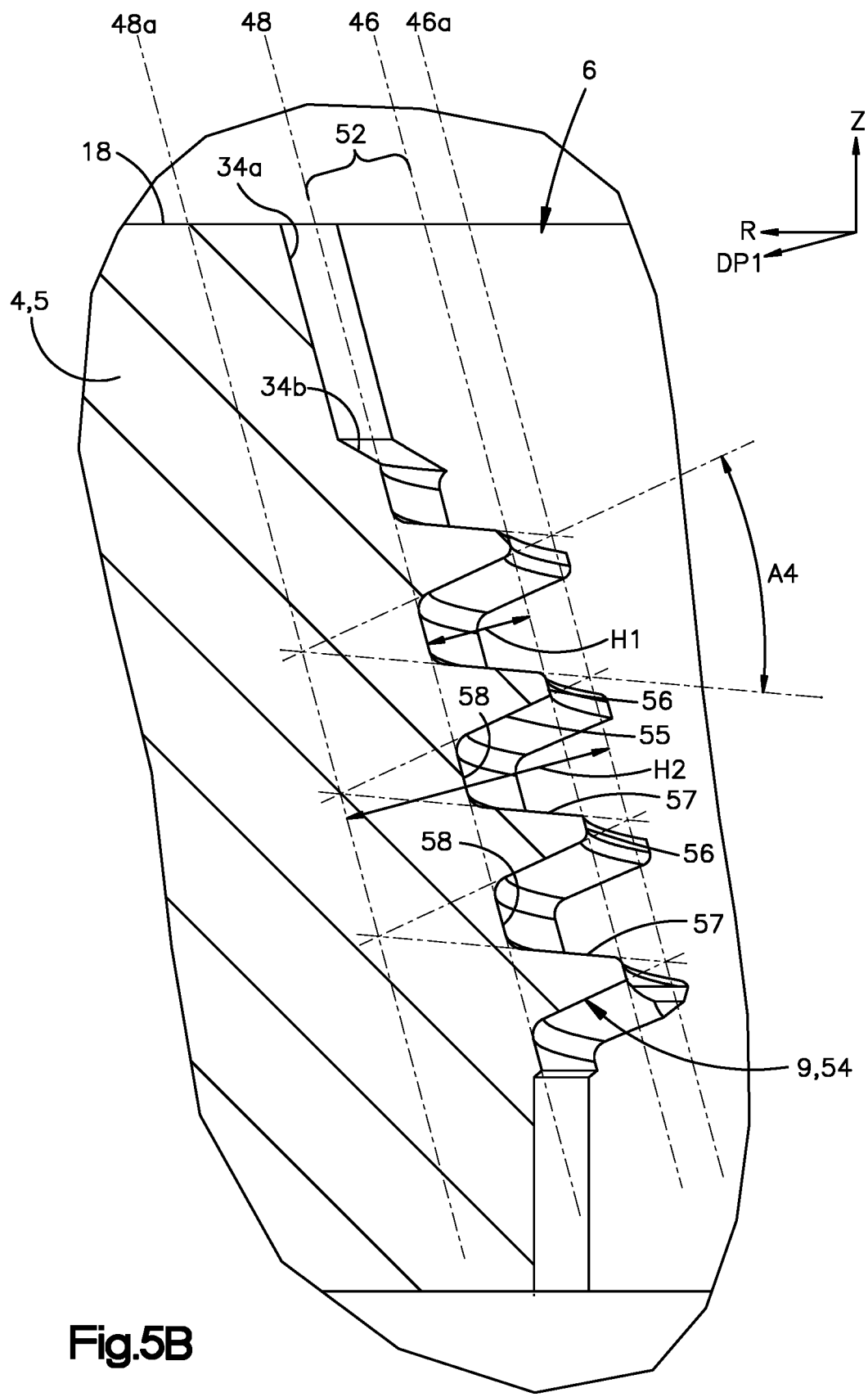
FIG. 5B is an enlarged sectional view of the threaded locking structure of the locking hole illustrated in FIG. 5A.

Referring now to FIGS. 5A through 5D, an additional embodiment of the VA locking hole 6 is shown having, among other things, a thinner thread profile and larger recesses 28 than those of the preceding embodiment. As shown in FIG. 5A, the recesses 28 of the present disclosure define a recess radius R10 greater than that of the preceding embodiment, such that the recesses 28 of the present embodiment each have a horizontal profile that subsumes a majority of a circle. Accordingly, at least a portion of the first and second sides 44, 45 of each threaded column 26, particularly the portions contiguous with the first surface 42, can taper toward each other. As depicted, the VA locking hole 6 of the present embodiment can have three (3) threaded columns 26 and three (3) recesses 28 sequentially located circumferentially between the columns 26, although the present embodiment can have fewer than three (3) or more than three (3) columns 26 and recesses 28. As shown in FIG. 5B, the hole 6 can also have a first lead in surface 34a that is steeper than the lead in surface 34 of the preceding embodiment. A second, lower lead in surface 34b can be contiguous with the first lead in surface 34a, an can be oriented at a shallower angle relative to the first lead in surface 34a.

Figure 5C:
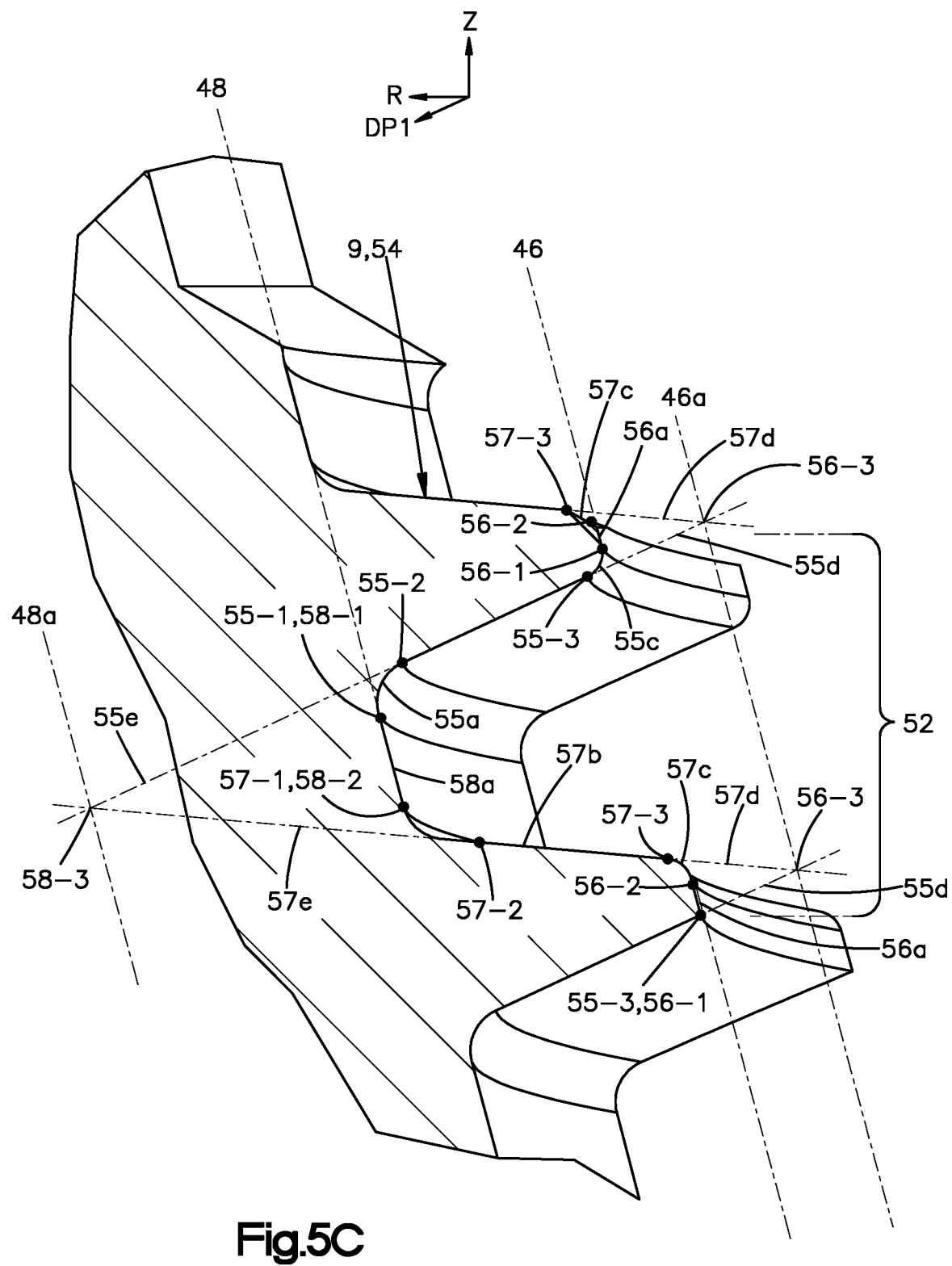
FIG. 5C is a sectional side view of a threaded head of another VA locking screw, which is configured to be locked at least with the locking hole illustrated in FIG. 5A.

Referring now to FIGS. 5B and 5C, as above, the crests 56 of the column threads 54 extend along the crest trajectory axis 46, and the roots 58 of the column threads extend along the root trajectory axis 48. Also, the column threads 54 define a thread angle A4 measured between the upper flank 55 and the lower flank 57 of a thread segment 52. In addition to having thinner profiles, the column threads 54 of the present embodiment define a single thread angle A4, which can be in a range of about 25 degrees to about 35 degrees, and can also be in a range of about 20 degrees to about 50 degrees, and can further be in a range of about 15 degrees to about 75 degrees. The column threads 54 of the present embodiment define a thread height H1 and a reference height H2. As above, the thread height H1 represents the actual thread height of the column threads 54, while the reference height H2 represents the theoretical maximum thread height comprising un-truncated crests 56 and un-relieved roots 58. At any of the thread segments 52, the thread height H1 is measured from the crest trajectory axis 46 to the root 58 along the direction DP1 perpendicular to the crest trajectory axis 46, while the reference height H2 is measured from the crest reference axis 46a to the root reference axis 48a along direction DP1.

As shown in FIG. 5C, the roots 58 of the present embodiment define elongated root profiles 58a that extend linearly along the root trajectory axis 48, which increases the total area between the opposed flanks 55, 57. This increases area between the flanks 55, 57, in combination with the thinner thread profiles, allows the column threads 54 to have beneficial malleability (and thus deformability) when engaged with the screw head threads 29. Furthermore, with reference to a radially inward direction, the profile of the upper flank 55 includes:

a) a first upper flank portion 55a (or upper "root relief" portion 55a) that extends from a first upper flank reference point 55-1 to a second upper flank reference point 55-2;
b) a second or "primary" upper flank portion 55b that extends along a consistent geometry from the second upper flank reference point 55-2 to a third upper flank reference point 55-3; and
c) a third upper flank portion 55c (or upper "crest relief" portion 55c) that extends from the third upper flank reference point 55-3 to a lower crest reference point 56-1.

Similarly, with reference to the radially inward direction, the profile of the lower flank 57 includes:

a) a first lower flank portion 57a (or lower "root relief" portion 57a) that extends from a first lower flank reference point 57-1 to a second lower flank reference point 57-2;
b) a second or primary lower flank portion 57b that extends along a consistent geometry from the second lower flank reference point 57-2 to a third lower flank reference point 57-3; and
c) a third lower flank portion 57c (or lower "crest relief" portion 57c) that extends from the third lower flank reference point 57-3 to an upper crest reference point 56-2.

In the present embodiment, the root profile 58a extends from an upper root reference point 58-1, which is coincident with the first upper flank reference point 55-1, to a lower root reference point 58-2, which is coincident with the first lower flank reference point 57-1. As before, the upper and lower root relief portions 55a, 57a can each be arcuate and define a root relief radius for reducing reduce stress concentrations at the root 58. Additionally, in the present embodiment, the upper and lower crest relief portions 55c, 57c can be arcuate and define a crest relief radius for reducing stress concentrations at the crest 56. As shown, one or more of the thread segments 52 of the present embodiment can have a primary flank profile portion 55b, 57b that extends to the respective upper or lower crest reference point 56-1, 56-2. Stated differently, one or more of the crests 56 need not have both upper and lower crest relief portions 55c, 57c. Moreover, as above, a transition portion, which can be arcuate, can optionally extend between the primary flank portions 55b, 57b and the respective third upper and lower flank portions 55c, 57c of any and up to all of the profiles flanks 55, 57.

As above, the crest reference axis 46a intersects crest reference points 56-3 of the reference profile, and the root reference axis 48a intersects root reference points 58-3 of the reference profile. Also similarly as described above, when the primary flank portions 55b, 57b are linear, the crest reference points 56-3 and the root reference points 58-3 can also be defined by respective intersections of the projections 55d, 57d and 55e, 57e of the primary flank portion 55b, 57b along their consistent geometries.

In the present embodiment, the thread height H1 can be in a range substantially equivalent to that described above with reference to FIG. 2G. Additionally, the plate thread height factor (HF-P) of the present embodiment can be in a range of about 0.36 to about 0.40, and can also be in a range of about 0.34 to about 0.70, and can further be in a range of about 0.30 to about 1.00. It should be appreciated that the elongated root profile 58a of the present embodiment effectively moves the root reference axis 48a further away from the central hole axis 22 relative to the preceding embodiment, which can also reduce the plate thread height factor (HF-P) relative to the preceding embodiment.

Figure 5D:
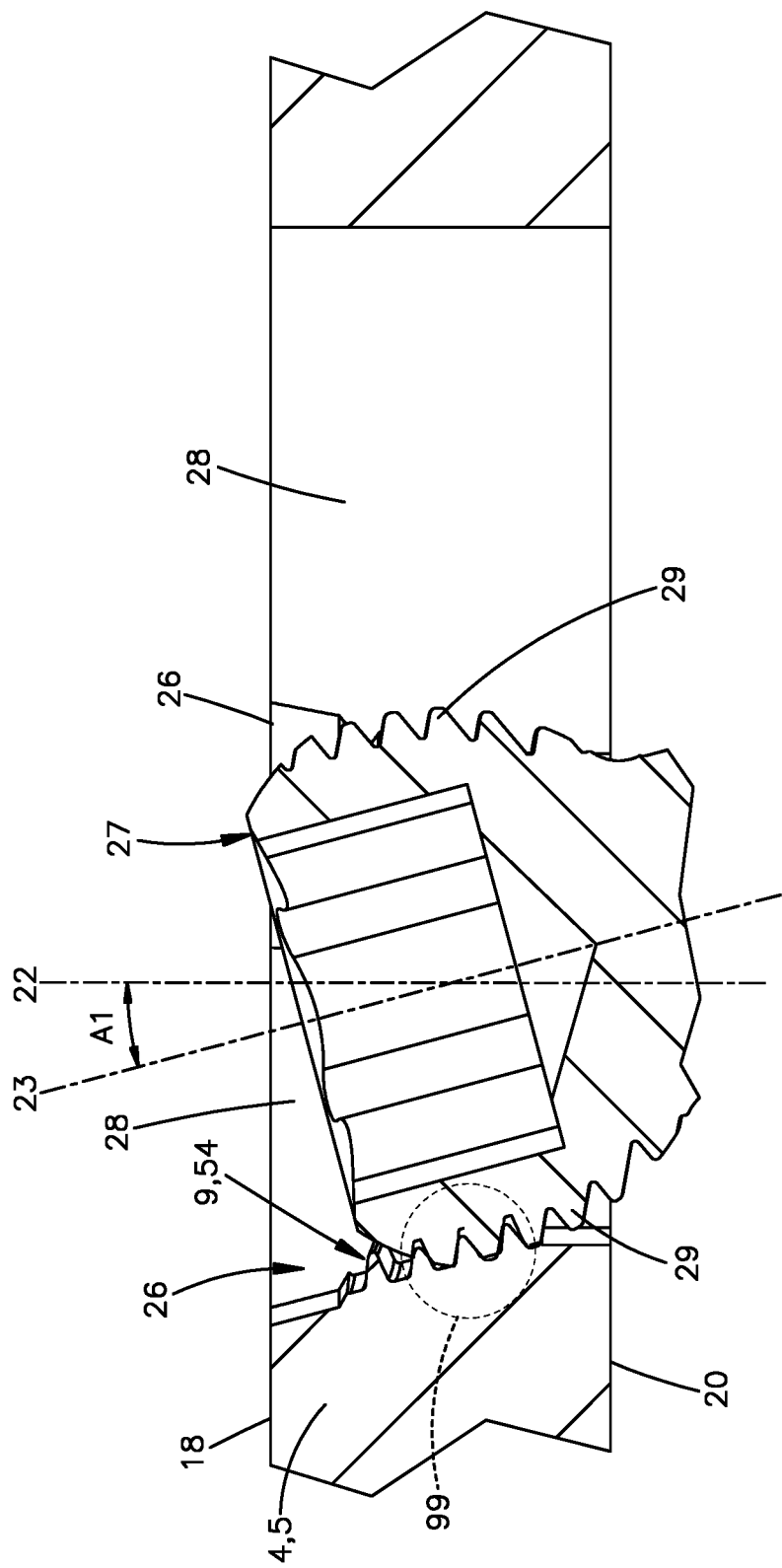
FIG. 5D is a sectional side view of the head of the VA locking screw illustrated in FIG. 5C in locking engagement with the locking hole illustrated in FIG. 5A.

Referring now to FIG. 5D, the thinner thread profiles of the present embodiment can also provide enhanced locking with the VA screw head 27, including advantageous thread deformation and enhanced mechanical locking strength, compared to prior art thread designs. Although the column threads 54 of the present embodiment might not provide as much radial clearance between the column thread roots 58 and the crests 76 of the screw head threads 29 as the preceding embodiment, the thinner profiles of the column threads 54 of the present embodiment can allow the column threads 54 to deform more readily upon engagement with the screw head threads 29, including at angulated screw insertion trajectories. For example, as shown in FIG. 5D, at angulation (such as an angulation A1 of about 15 degrees), the column threads 54 can deform favorably in the radial direction R (as well as along direction DP1) at their crests 56 and flanks 55, 57 responsive to engagement with the screw head threads 29 at interference region 99. Additionally, the upper and lower flanks 55, 57 of the column threads 54 are generally positioned at complimentary orientations with the upper and lower flanks 75, 77 of the screw head threads 29 at angulation, which provides a beneficial form fit at angulation. As above, by interfacing the stronger profiles of the screw head thread threads 29 against the thinner, malleable profile of the column threads 54 of the present embodiment, the vast majority of the thread deformation can be imparted to the plate threads 9, allowing the plate threads 9 to deform so as to effectively re-align to the angulated central screw axis 23. Additionally, the foregoing deformation, as above, occurs primarily radially outward, although some measure of axial and/or circumferential deformation can occur (mostly when a timing-error is present).

Figure 6A:
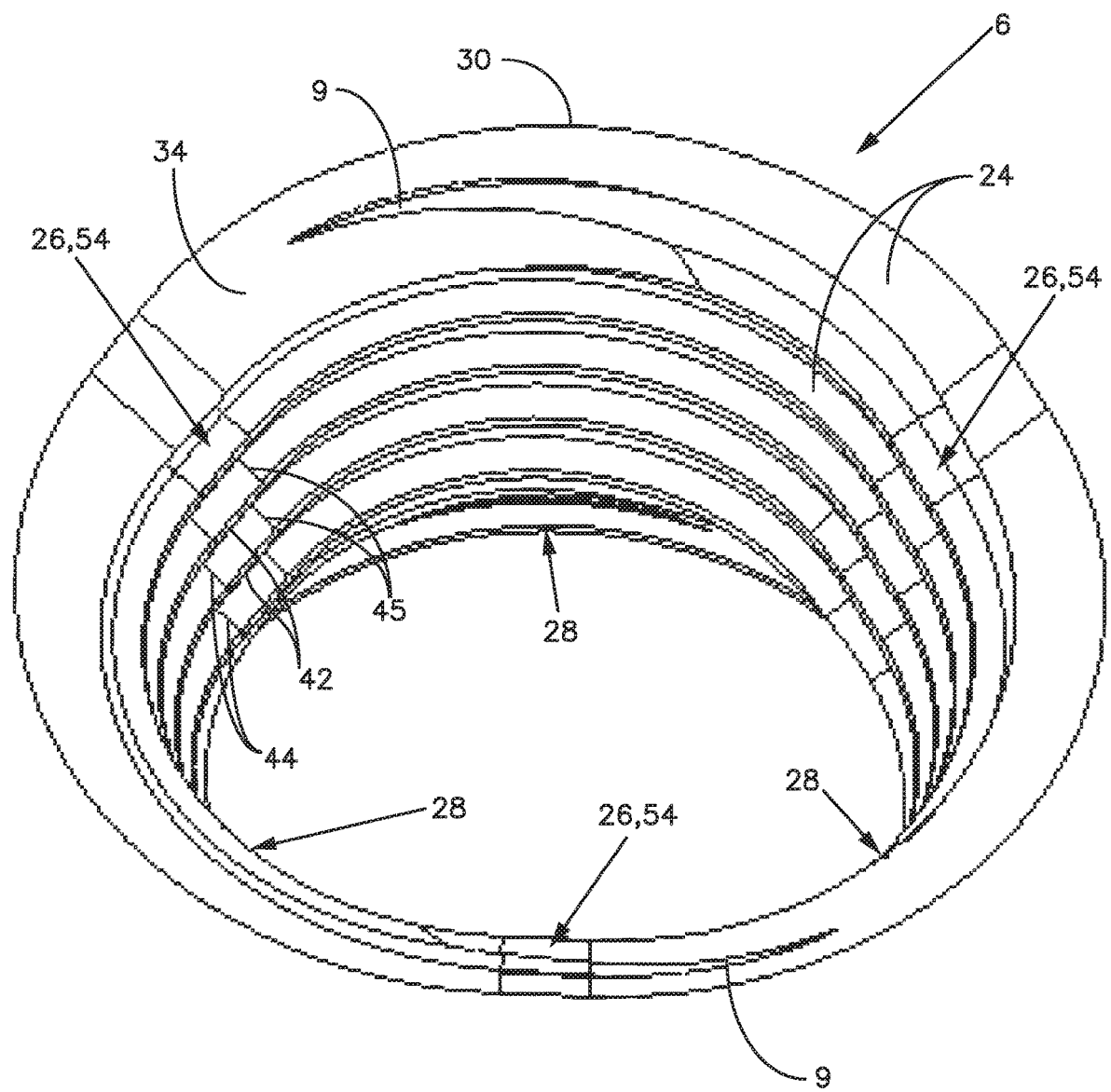
FIG. 6A is a perspective view of another locking hole, which has a trigon horizontal hole profile, and includes a threaded locking structure defined by an interior surface of the locking hole, according to an additional embodiment of the present disclosure.
Figure 6B:
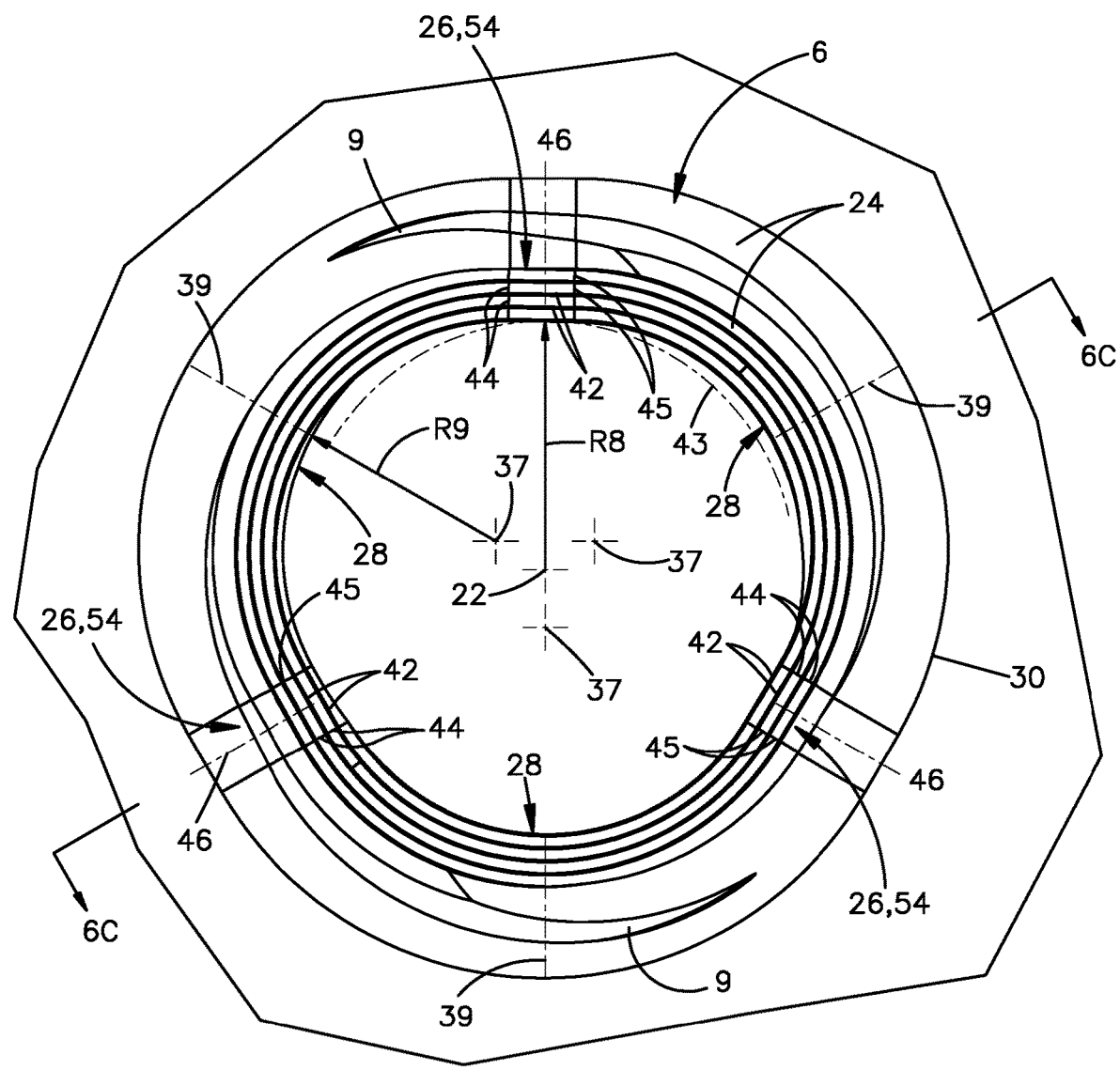
FIG. 6B is a top view of the locking hole illustrated in FIG. 6A.

Referring now to FIGS. 6A and 6B, in additional embodiments, the VA locking hole 6, or at least an axial portion thereof, can have a horizontal hole profile that is non-circular. By way of non-limiting example, at least an axial portion of the hole 6 can have a generally polygonal horizontal hole profile. In particular, the present embodiment of the VA locking hole 6 is shown having a trigon (i.e., generally triangular) horizontal profile, although other polygonal shapes are within the scope of the present disclosure. The interior surface 24 of the plate body 5 within the hole 6, or at least an axial portion thereof, defines a corresponding non-circular (e.g., trigon) horizontal profile. Additionally, plate threads 9 extend along a thread path that has a corresponding non-circular (e.g., trigon) horizontal profile. Moreover, one or more and up to each of the upper perimeter 30, the one or more lead in surfaces 34, the one or more undercut surfaces 36, and the lower perimeter 32 of the hole 6 can also have corresponding non-circular (e.g., trigon) horizontal profiles.

In the illustrated embodiment, the first surfaces 42 of the columns 26 have linear horizontal profiles. In other embodiments, one or more of the first surfaces 42 can have arcuate profiles having a relatively large radii. In either of such embodiments, the first surfaces can tangentially intersect a reference circle 43 centered at the central hole axis 22. In particular, the first surfaces 42 can intersect the reference circle 43 substantially at the crest trajectory axis 46. Is should be appreciated that the reference circle 43 illustrates the hole's departure from a circular horizontal profile. The reference circle 43 in FIG. 6B is shown intersecting an axially lowermost one of the first surfaces 42 within the polygona hole 6, at which axial location the reference circle 43 also illustrates the minimum diameter within the hole 6 (and thus also the minimum minor diameter of the plate threads 9). The reference circle 43 defines a radius R8, which, for the depicted reference circle 43, is equivalent to one-half (½) the minimum minor thread diameter of the hole 6. For the depicted reference circle 43, the radius R8 can be in a range of about 2.0 mm to about 2.1 mm, and can also be in a range of about 1.8 mm to about 2.5 mm. In additional embodiments, including those for use with VA locking screws 8 with screw shafts 25 having a major diameter in a range of about 1.0 mm to about 5.0 mm, radius R8 can be in a range of about 0.5 mm to about 3.5 mm. It should be appreciated that radius R8 can optionally be used as a metric for categorizing the size of the hole 6 (for example, as an alternative of, or in addition to, any of the mean crest radius R2, the mean radius R3, and the mean root radius R4 described above). As above, the first surface 42 of each column 26 extends between a first side 44 and a second side 45, which sides 44, 45 define interfaces between the column 26 and the circumferentially adjacent recesses 28. In the present embodiment, however, the recesses 28 extend tangentially from the first and second sides 44, 45 of the associated columns 26. In this manner, the first surfaces 42 of the columns 26 effectively define the sides of the trigon, while the recesses 28 effectively define the corners of the trigon, each as viewed in the horizontal reference plane. Accordingly, the recesses 28 of the present embodiment can also be referred to as "corners" 28. Each of the corners 28 can define a corner radius R9, measured from the corner axis 37 to the corner apex 39. The corner radii R9 can be in a range from about 0.0 mm to marginally smaller than R8 and further to about R8. The crests 56 and roots 58 of the plate threads 9 extend along respective splines that revolve about the central hole axis 22 helically along the trigon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, the plate threads 9 can circumferentially traverse the columns 26 and the corners 28 in an uninterrupted fashion (i.e., the plate threads 9 need not bottom-out in the corners 28). Accordingly, the plate threads 9 can transition smoothly and continuously between the column threads 54 and the portions of the threads 9 that traverse the corners 28.

In the present embodiment, the length of the first surfaces 42, and thus the distance between the sides 44, 45 of each column 26, can be substantially consistent within each column 26 as the thread path advances between the upper and lower surfaces 18, 20 of the plate 4. Alternatively, the length of the first surfaces 42 of each column 26 can successively increase as the thread path advances from the upper surface 18 toward the lower surface 20 of the plate 4, thereby causing the corner radii R9 to progressively decrease toward the lower surface 20 of the plate 4.

Referring now to FIG. 6C, the plate threads 9 of the present embodiment can have a substantially consistent thread profile and thread height H1 as the threads 9 revolve along their thread path(s) about central hole axis 22, including along one or more revolutions. Thus, the thread height H1 can be substantially equivalent at the crest centerlines 48 of the columns 26 and at the corner apices 39, and also at the portions of the columns 26 and corners 28 therebetween. As shown in FIG. 6C, the corner apices 39 can be defined along the crests 56 of the threads 9, and a corner root axis 39a can extend linearly in a manner intersecting the roots 58 of the threads 9. At the corner apex 39, the thread height H1 is measured between the crest 56 (or the corner apex 39) and the root 58 (or the corner root axis 39a) along a direction DP4 perpendicular to the corner apex 39. In the present embodiment, each corner apex 9 and corner root axis 39a shares a common axial plane with the crest trajectory axis 46 and root trajectory axis 48 of an opposed one of the columns 26. Thus, with respect to the thread profile, the recess apex 39 is analogous to the crest trajectory axis 46, while the corner root axis 39a is analogous to the root trajectory axis 48. Accordingly, the crest trajectory axis 46 and the corner apex 39 can each be oriented at angle A2 described above, while the root trajectory axis 48 and the corner root axis 39a can each be oriented at angle A3 described above.

Moreover, the plate threads 9 of the present embodiment can also define a helical series of thread segments 52 having substantially consistent thread profiles along the thread path(s), including at the crest centerlines 48, at the corner apices 39, and locations circumferentially therebetween. In particular, the crests 56, roots 58, and upper and lower flanks 55, 57 of the threads 9 of the present embodiment can each have substantially consistent profiles along the thread path(s). It is to be appreciated that, in the present embodiment, the crests 56 can define crest profiles 56a, the roots can define root profiles 58a, and the upper and lower flanks 55, 57 can define respective upper and lower flank profile portions 55a-c, 57a-c (including optional transition portions), each in a similar manner as those described above with reference to FIG. 2G. Accordingly, the threads 9 at the columns 26 and corners 28 can be multi-angle threads, including dual-angle threads, particularly with first and second thread angles A4, A5 as described above. Alternatively, the plate thread profiles of the present embodiment can be configured similarly to the single-angle threads described above with reference to FIGS. 5B through 5D, or can include arcuate thread profiles as described above with reference to FIGS. 2H and 2I. Moreover, the thread segments 52 of the column threads 54 also define a reference thread height H2 measured between a crest reference axis 46a and a root reference axis 48b, which are also defined in the manner described above with reference to FIG. 2G. It should be appreciated that the threads 9 of the corners 28 also define a reference height H2, which, at the corner apex 39, is measured along direction DP4 between an un-truncated crest reference point and an un-relieved root reference point, which are defined by the thread profiles at the corners in an analogous manner as described above with reference to FIG. 2G. It should also be appreciated that the thread height H1 and reference thread height H2 can be substantially equivalent at the columns 26 and corners, respectively, and can also be within the respective ranges described above.

It is to be appreciated that the trigon-shaped VA locking hole 6 described above increases the total contact area between the plate threads 9 and the screw head threads 29, while also providing the plate threads 9, particularly the column threads 54 thereof, with a measure of the favorable deformation qualities described above. In this manner, the locking interface of the plate threads 9 and screw head threads 29 can provide the locking screw 8 with an overall cantilever strength (i.e., resistance to a force applied perpendicularly to the central axis 23 of the screw 8) greater than that of the preceding embodiments, while also causing most if not substantially all of the thread deformation at the locking thread interface to be imparted plastically and elastically to the plate threads 9. The inventors have discovered, surprisingly and unexpectedly, through their own extensive testing, that the plate threads 9 of the present embodiment and the screw head threads 27 described above have a locking thread interface that, at certain angulations, has a cantilever strength that approaches and can even exceed the ultimate bending strength of the screw 8. For example, the inventors' tests have shown that a VA locking screw 8, configured as described above and fully seated in the VA locking hole 6 of the present embodiment at an angulation from nominal to about 6 degrees, will fail (i.e., break, or bend to an extent categorized as failure of a VA locking screw) at a location of the screw shaft 25 proximate the distal end 72 of the head 27. Stated differently, at the foregoing conditions, the screw shaft 25 will fail before the locking thread interface fails. Moreover, at a fully seated insertion at angulations in a range from about 6 degrees to about 15 degrees, the cantilever strength of the locking thread interface decreases to within a range of about 30 percent to 40 percent of the ultimate bending strength of the screw 8. These cantilever strengths of the locking thread interface, particularly at angulation, represent significant improvements over prior art VA locking hole-screw systems.

Figure 7A:
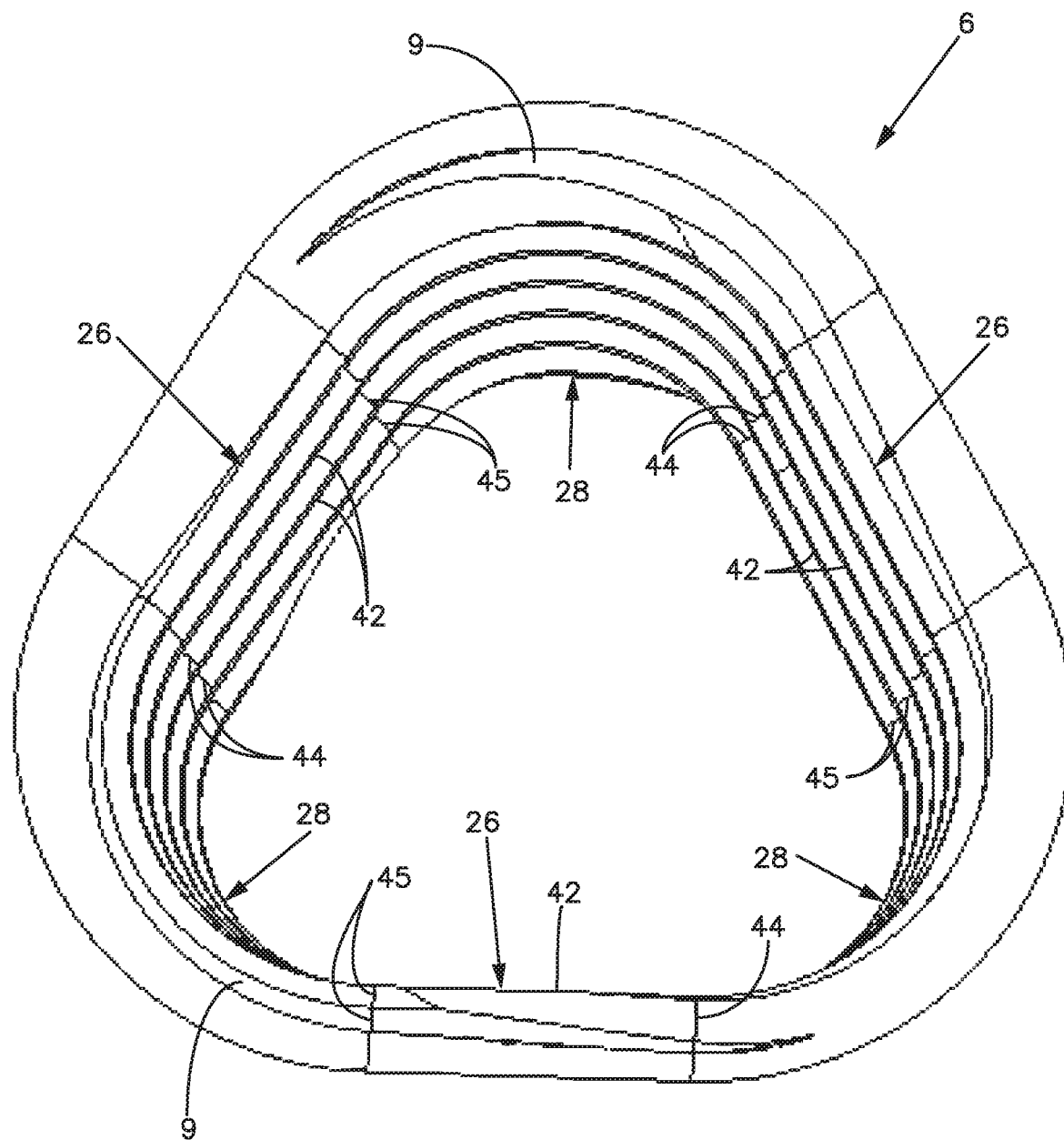
FIG. 7A is a perspective view of another locking hole, which has a trigon horizontal hole profile with smaller corner radii relative to the locking hole of FIG. 6A, and which includes a threaded locking structure defined by an interior surface of the locking hole, according to a further embodiment of the present disclosure.
Figure 7B:
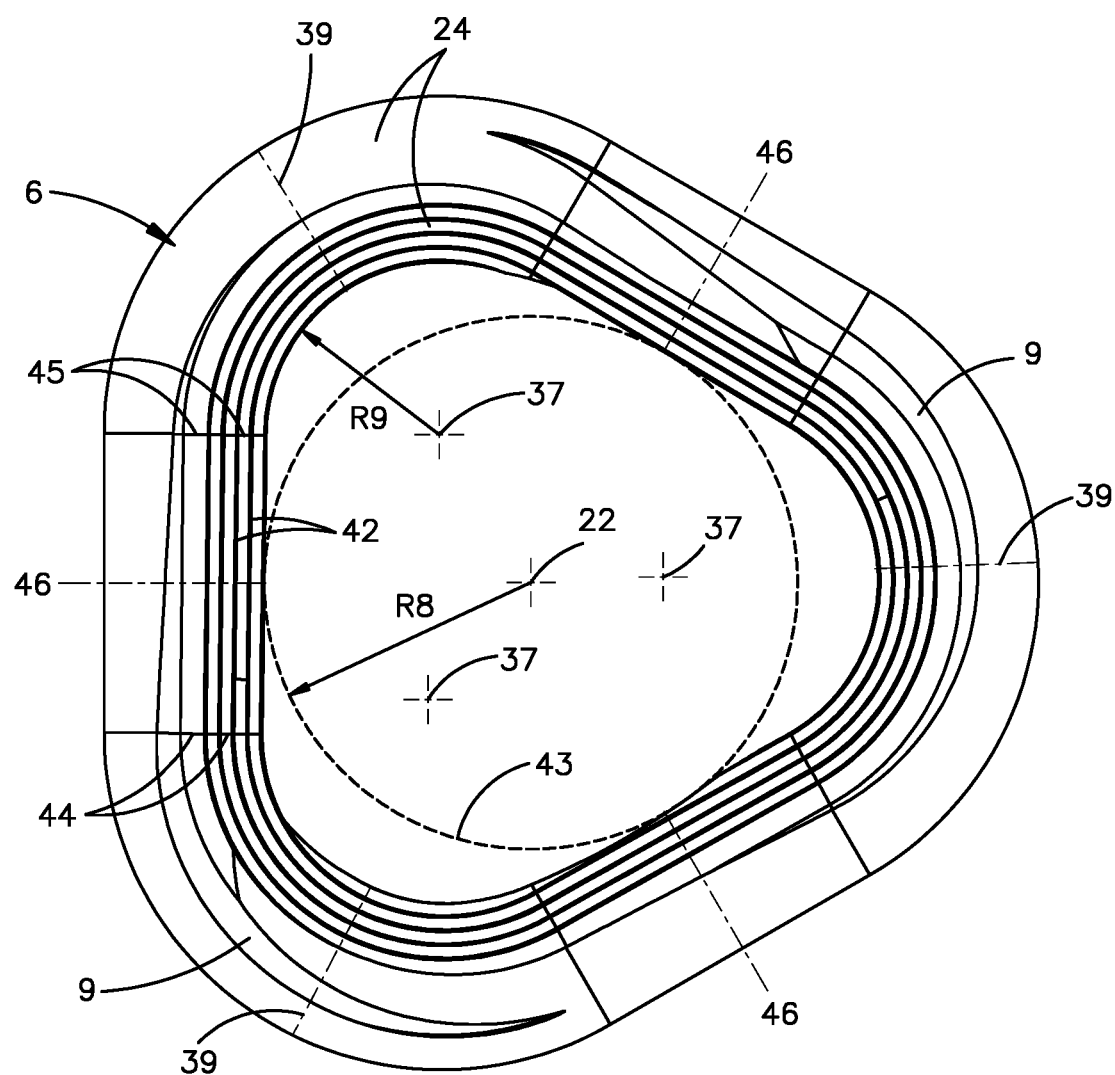
FIG. 7B is a top view of the locking hole illustrated in FIG. 7A.

Referring now to FIGS. 7A and 7B, in further embodiments, the corner radii R9 of the polygonal-shaped (e.g., trigon-shaped) VA locking hole 6 can be reduced and the length of the first surfaces 42 of the thread columns 26, as measured between the sides 44, 45, can be increased, thereby providing the polygonal hole 6 with sharper corners 28, and thus a more profound polygonal (e.g., triangular) shape. Accordingly, the plate threads 9, and thus the crests 56 and roots 58 thereof, can extend along a thread path that also has a more profound triangular shape as it traverses the columns 26 and corners 28. The other parameters of the trigon-shaped hole 6 can be maintained as described above with reference to FIGS. 6A through 6C, including the radius R8 of the reference circle 43, the axial taper angles A2, A3, the thread profiles, the thread angles A4, A5, the thread height H1, and the reference height H2. Alternatively, one or more of these other parameters can be adjusted as needed.

It is to be appreciated that reducing the corner radii R9 and increasing the length of the first surfaces 42 of the polygonal-shaped VA locking hole 6 effectively distributes forces between the plate threads and the screw head threads 29 in a more tangential manner relative to the force distribution of the polygon-shaped locking hole 6 described above with reference to FIGS. 6A through 6C.

Figure 8A:
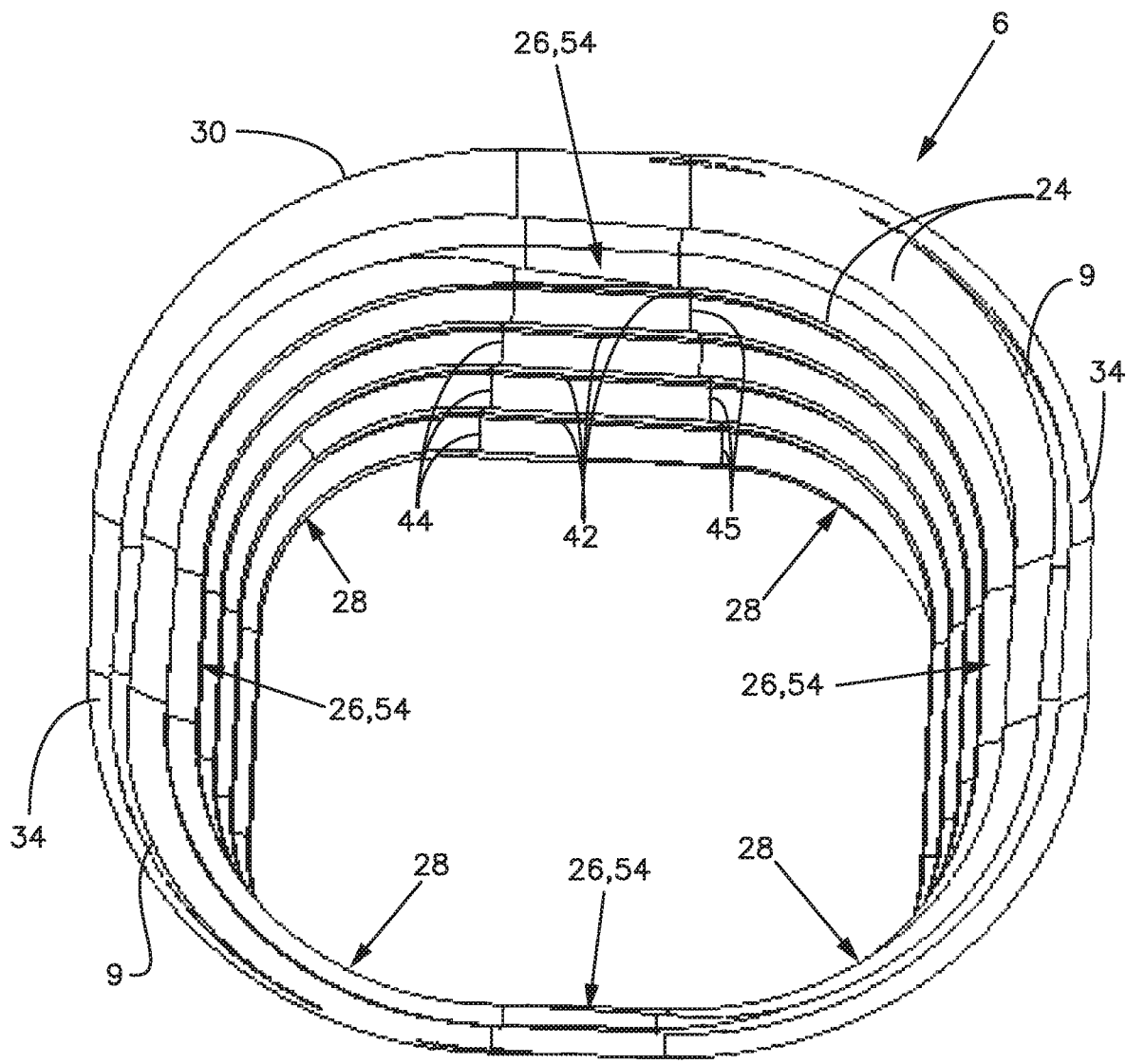
FIG. 8A is a perspective view of another locking hole, which has a tetragon horizontal hole profile, and which includes a threaded locking structure defined by an interior surface of the locking hole, according to yet another embodiment of the present disclosure.
Figure 8B:
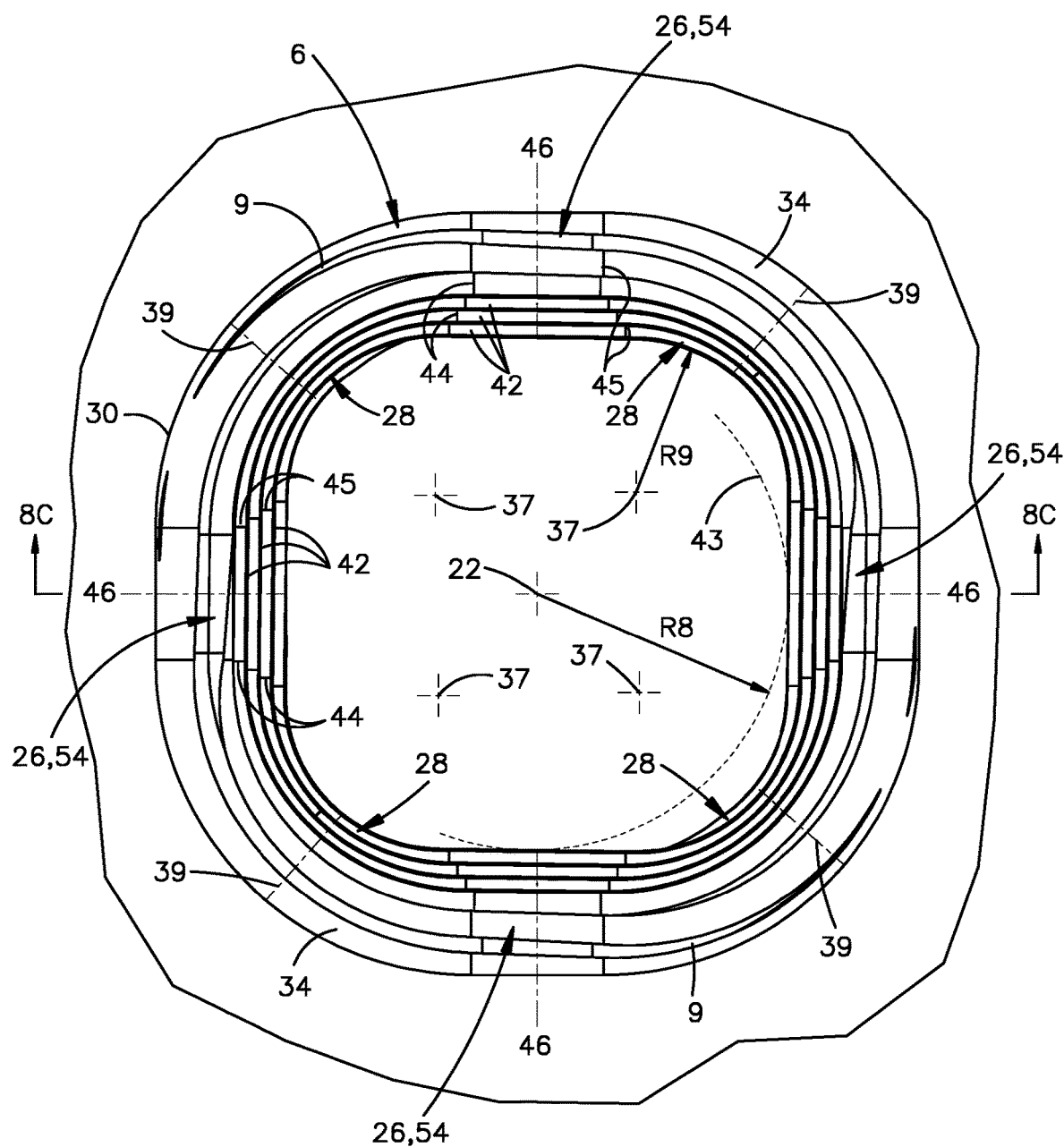
FIG. 8B is a top view of the locking hole illustrated in FIG. 8A.

Referring now to FIGS. 8A and 8B, in additional embodiments, the VA locking hole 6 can have a polygonal horizontal profile in the shape of a tetragon (i.e., a four-sided polygon). Accordingly, the interior surface 24 of the plate body 5 within the hole 6 defines a corresponding tetragon horizontal profile. Additionally, the upper perimeter 30, the one or more lead in surfaces 34, the one or more undercut surfaces 36, and the lower perimeter 34 of the hole 6 preferably can also have corresponding tetragon horizontal profiles.

As in the polygonal-shaped holes described above, the first surfaces 42 of the columns 26 have linear horizontal profiles that tangentially intersect the reference circle 43. In particular, each of the first surfaces 42 intersects the reference circle 43 substantially at the crest trajectory axis 46. The radius R8 of the reference circle 43 can be within the ranges described above. The corners 28 extend tangentially from the first and second sides 44, 45 of each column 26, such that the first surfaces 42 define the sides of the tetragon extending between the corners 28. In the present embodiment, the corner radii R9 can be in any of the ranges described above with reference to FIGS. 6A through 7C.

In the present embodiment, the length of the first surfaces 42, and thus the distance between the sides 44, 45 of each column 26, can successively increase as the thread path advances toward the lower surface 20 of the plate 4. Accordingly, the respective engagement forces between the plate threads 9 and the screw head threads 29 can be progressively distributed in a more tangential manner as the screw head 27 advances within the hole 6, including at an angulated insertion trajectory. Alternatively, the first surfaces 42 of each column 26 can have a substantially consistent length along the thread path.

Similar to the manner described above, the crests 56 and roots 58 of the plate threads 9 extend along respective splines that revolve about the central hole axis 22 helically along the tetragon profile of the interior surface 24 between the upper plate surface 18 and the lower plate surface 20. Additionally, the interior surface 24, including the columns 26 as well as the corners 28, tapers inwardly toward the central hole axis 22 from the upper plate surface 18 toward the lower plate surface 20. Moreover, as shown, the plate threads 9 can circumferentially traverse one or more an up to each of the corners 28 in an uninterrupted fashion (i.e., the plate threads 9 need not bottom-out in the corners 28).

Figure 8C:
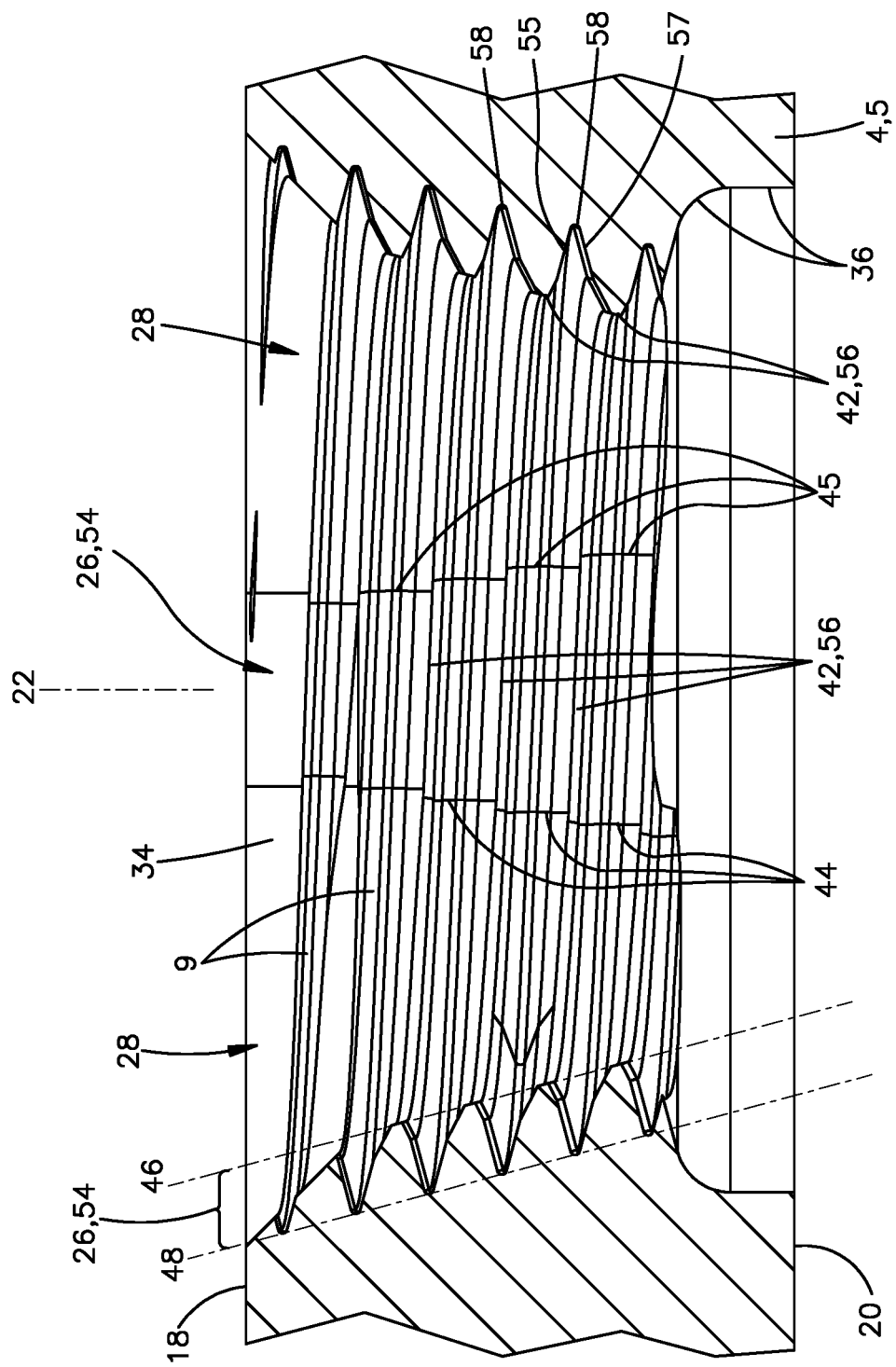
FIG. 8C is a sectional side view of the locking hole taken along section line 8C-8C shown in FIG. 8B, illustrating the threaded locking structure of the hole.

Referring now to FIG. 8C, the plate threads 9 of the present embodiment can define thread profiles similar to those described above with reference to FIG. 2G, as well as with reference to the trigon-shaped VA locking holes 6. Moreover, it should be appreciated that the thread profiles, including the crest 56, roots 58, and flanks 55, 57 thereof, can be substantially consistent along the thread path, including at the columns 26 and at the corners 28, as described above with reference to the trigon-shaped holes 6. Accordingly, the threads 9 can have a substantially consistent thread height H1, as well as a substantially consistent reference height H2, along the thread path(s). The thread height H1 and reference height H2 can be defined as described above.

As with the trigon-shaped VA locking holes 6 described above, the tetragon-shaped holes 6 of the present embodiment effectively increase the total contact area between the plate threads 9 and the screw head threads 29, while also providing the threads 9 with a measure of the favorable deformation qualities described above. In this manner, the locking thread interface of the tetragon-shaped hole 6 can exhibit an overall cantilever strength greater than that of the embodiments described above with reference to FIGS. 2A through 2G and 4A through 5D.

It should be appreciated that the VA locking holes 6 of the present disclosure can have other polygonal horizontal profiles, including pentagonal (i.e., five sides 42 and five corners 28), hexagonal (i.e., six sides 42 and six corners 28), heptagonal (i.e., seven sides 42 and seven corners 28), octagonal (i.e., eight sides 42 and eight corners 28), nonagonal (i.e., nine sides 42 and nine corners 28), decagonal (i.e., ten sides 42 and ten corners 28), etc. It should also be appreciated that in any of the polygonal-shaped VA locking holes 6 of the present application, the threads 9 can extend in continuous and un-interrupted fashion along the columns 26 and corners 28, or optionally the threads 9 can bottom-out in the corners 28. Moreover, the thread profiles in any of the non-circular (e.g., polygonal-shaped) VA locking holes 6 of the present application can be single-angle (e.g., similar to that described above with reference to FIGS. 5B through 5D), dual-or additional multi-angle, or arcuate, as described above.

In additional embodiments, the VA locking holes 6 of the present disclosure can have multiple horizontal hole profiles (i.e., hole shapes) along the central hole axis 22. For example, the internal surface 24 within any of the VA locking holes 6 can optionally include at least a first axial portion adjacent the upper plate surface 18 and defining a first horizontal hole profile and at least a second axial portion extending axially between the first axial portion and the lower plate surface 20 and defining a second horizontal hole profile that is different than the first horizontal hole profile. By way of one non-limiting example, the first axial portion of the interior surface 24 can extend from the upper perimeter 30 of the hole 6 and can include the lead-in surface(s) 34 and the threads 9 having a fully-developed thread-form, while the second axial portion of the interior surface 24 can include the undercut surface 36 and can extend to the lower perimeter 32 of the hole 6. The first axial portion can have any of the circular or non-circular horizontal profiles described herein (including any of the polygonal profiles), while the second axial portion can have any of the foregoing profiles that is different than the first axial portion. In such multi-profile hole embodiments, the interior surface 24 can also include a transition portion between the first and second axial portions, in which the horizontal hole profile transitions between the first and second horizontal hole profiles. It should be appreciated that the interior surface 24 can also include one or more additional axial portions each having a horizontal hole profile that is different than at least one other of the horizontal hole profiles within the VA locking hole 6.

Figure 9:
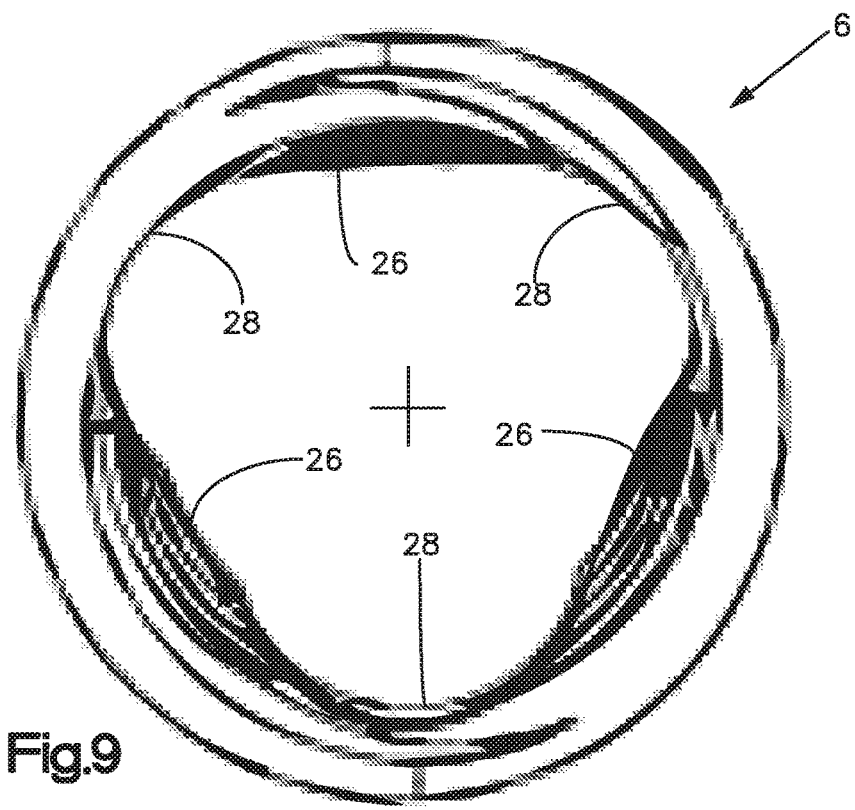
FIG. 9 is a top view of a locking hole having three (3) threaded locking structures and three (3) recesses, and otherwise being configured similarly to the locking hole shown in FIG. 2D.
Figure 10:
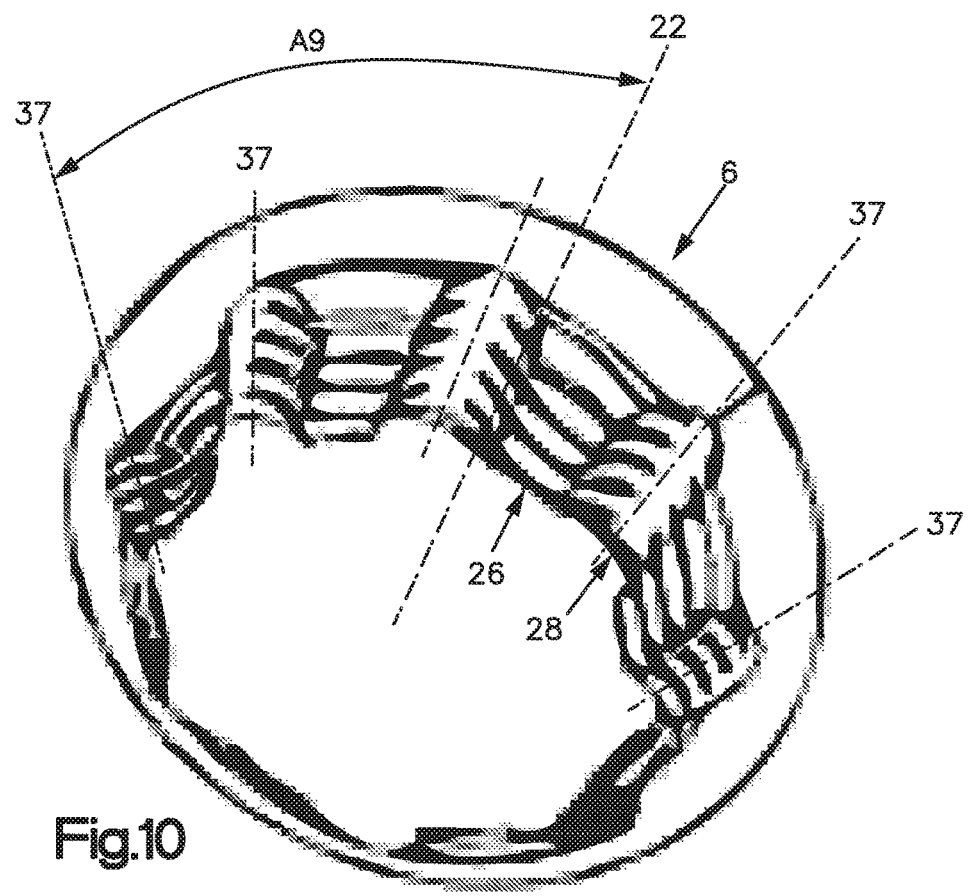
FIG. 10 is a perspective view of another locking hole having eight (8) threaded locking structures and eight (8) recesses, according to another embodiment of the present disclosure.

Furthermore, as mentioned above, the design of the VA locking hole 6 is not limited by the number of columns and recesses or corners 28. Accordingly, by way of a non-limiting example, the hole 6 can have three (3) columns 26 circumferentially spaced between three (3) recesses 28, as shown in FIG. 9. Moreover, the hole 6 can alternatively have more than four (4) each of columns 26 and recesses 28. In further embodiments, the VA locking hole 6 can have five (5), six (6), seven (7), eight (8), nine (9), ten (10), eleven (11), twelve (12), thirteen (13), fourteen (14), fifteen (15), sixteen (16), or more than sixteen (16) each of columns 16 and recesses 28. By way of another non-limiting example, FIG. 10 shows a VA locking hole 6 having eight (8) columns 26 circumferentially spaced between eight (8) recesses 28. Additionally, as shown, the recesses 28 can define central recess axes 37 that are oriented at an acute angle A9 with respect to the central hole axis 22. In such embodiments, the angle A9 can be substantially equivalent to the angle A2 at which the crest trajectory axis 46 is oriented, as described above with reference to FIG. 2E.

It should also be appreciated that any of the VA locking holes 6 described above can be incorporated into a combination hole (also referred to as a "combi-hole") within the bone plate 4. Such a combi-hole includes a compression hole in combination with one of the VA locking holes 6 described above, whereby the interior surface 24 of the plate body 5 can define both the VA locking hole 6 and the compression hole 92, each extending from the upper plate surface 18 to the lower plate surface 20. Additional details of the combi-hole, as well as operation of a compression screw in the combination hole portion thereof, can be as more fully described in the '761 and '047 References.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone fixation system, comprising:
a bone plate having a body that defines an interior surface that defines at least one hole that defines a central axis, the interior surface defining plate threads; and
a bone screw having a head and a shaft extending from the head along a central axis of the bone screw, the head having an exterior surface that defines head threads that are configured to threadedly engage the plate threads, wherein the plate threads and the head threads each have a cross-sectional profile in a respective reference plane extending along the respective central axis, the cross-sectional profiles each comprising:
roots;
crests; and
flanks extending from the roots toward the crests, wherein the roots, crests, and flanks collectively deviate from a reference cross-sectional profile that is V-shaped in the respective reference plane and defines crest reference points at apices at a first side thereof and root reference points at apices at a second side thereof opposite the first side,
such that a thread height measured from the crests to the roots is less than a reference height measured from the crest reference points to the root reference points,
wherein a first ratio of the thread height of the head threads to the reference height of the head threads is in a range of 0.50:1 to 0.80:1, and a second ratio of the thread height of the plate threads to the reference height of the plate threads is in a range of 0.50:1 to 1.00:1.

2. The bone fixation system of claim 1, wherein the bone screw is formed of a material selected from the group comprising stainless steel, titanium, a titanium-aluminum-niobium (TAN) alloy, a titanium-aluminum-vanadium (TAV) alloy, and a cobalt-chrome alloy.

3. The bone fixation system of claim 2, wherein the bone plate is formed of a material selected from the group comprising stainless steel, titanium, a titanium-aluminum-niobium (TAN) alloy, a titanium-aluminum-vanadium (TAV) alloy, a cobalt-chrome alloy, and nitinol.

4. The bone fixation system of claim 1, wherein the flanks of the plate threads define a plate thread angle in a range of about 20 degrees to about 60 degrees.

5. The bone fixation system of claim 4, wherein the flanks of the head threads define a head thread angle in a range of about 30 degrees to about 55 degrees.

6. The bone fixation system of claim 5, wherein a ratio of the thread height of the plate threads to the thread height of the head threads is in a range of 1.0:1 to 2.0:1.

7. The bone fixation system of claim 5, wherein the flanks of the plate threads have a first portion that defines the thread angle and a second portion that defines a second thread angle, wherein the second portions of the flanks are located between the first portions and the crests, respectively, the thread angle is in a range of about 25 degrees to about 40 degrees, and the second thread angle is in a range of about 40 degrees to about 120 degrees.

8. The bone fixation system of claim 7, wherein the first and second portions are substantially linear.

9. The bone fixation system of claim 4, wherein the flanks of the plate threads are arcuate.

10. The bone fixation system of claim 1, wherein the crests of the head threads each define relieved crest profiles in the respective reference plane.

11. The bone fixation system of claim 10, wherein at least some of the relieved crest profiles of the heads threads are rounded and define a radius in a range of about 0.06 mm to about 0.25 mm.

12. The bone fixation system of claim 11, wherein rounded crest profiles of the head threads define a crest width that is 0.05 mm or greater.

13. The bone fixation system of claim 12, wherein crests of the head threads are defined at apices of the rounded crest profiles, and the cross-sectional profile of the head threads defines an arcuate crest trajectory axis that intersects the apices of the rounded crest profiles.

14. The bone fixation system of claim 1, wherein the crests of the plate threads are coincident with a crest trajectory axis that is linear in the respective reference plane.

15. The bone fixation system of claim 14, wherein the crest trajectory axis is oriented at an angle in a range of about 5 degrees to about 30 degrees relative to the central axis of the hole.

16. The bone fixation system of claim 14, wherein the crests of the plate threads define linear crest profiles that extend along the crest trajectory axis extending in the respective reference plane.

17. The bone fixation system of claim 14, wherein the crests of the plate threads define rounded crest profiles.

18. The bone fixation system of claim 1, wherein the interior surface further defines:
   a plurality of columns sequentially located about a circumference of the interior surface, wherein the plate threads traverse each of the columns; and
   a plurality of recesses located circumferentially between the columns.

19. The bone fixation system of claim 18, wherein the thread height and the reference height are substantially constant within each of the columns along at least one revolution about the central axis of the hole.

20. The bone fixation system of claim 18, wherein each of the columns defines a plurality of first surfaces that extend from a first side of the column to a second side of the column, the first surfaces define the crests, wherein, in a second reference plane that is orthogonal to the central axis of the hole, each of the recesses extends tangentially from the first side of one of the columns to the second side of an adjacent column, the first surfaces of the columns are symmetrically oriented about the central axis of the hole, and the recesses have a substantially common radius in the second reference plane.

21. The bone fixation system of claim 20, wherein the interior surface defines three columns and three recesses, such that at least an axial portion of the interior surface through which the second reference plane extends defines a trigonal profile in the second reference plane.

22. The bone fixation system of claim 20, wherein at least an axial portion of the interior surface through which the second reference plane extends defines a quantity of columns and recesses selected from the group comprising:
   four columns and four recesses, such that the at least an axial portion of the interior surface defines a tetragonal profile in the second reference plane;
   five columns and five recesses, such that the at least an axial portion of the interior surface defines a pentagonal profile in the second reference plane; and
   six columns and six recesses, such that the at least an axial portion of the interior surface defines a hexagonal profile in the second reference plane.

23. The bone fixation system of claim 20, wherein the plate threads traverse each of the columns and recesses such that the thread height and the reference height are substantially constant along each of the columns and recesses along at least one revolution about the central axis of the hole.

* * * * *